United States Patent [19]

Hardy et al.

[11] Patent Number: 4,977,166
[45] Date of Patent: Dec. 11, 1990

[54] BENZOPYRAN DERIVATIVES AND PHARMACEUTICAL COMPOSITIONS CONTAINING THEM

[75] Inventors: Jean-Claude Hardy, Cergy; Christian Renault, Taverny, both of France

[73] Assignee: Rhone-Poulenc Sante, France

[21] Appl. No.: 327,093

[22] Filed: Mar. 22, 1989

Related U.S. Application Data

[63] Continuation-in-part of Ser. No. 222,613, Jul. 21, 1988, abandoned.

[30] Foreign Application Priority Data

Jul. 23, 1987 [FR] France ............... 87 10453

[51] Int. Cl.$^5$ ............... A61K 31/495; C07D 405/06
[52] U.S. Cl. ............... 514/323; 514/318; 514/320; 514/321; 546/194; 546/196; 546/197; 546/201; 544/364; 544/393; 544/376; 544/377
[58] Field of Search ............... 544/364, 373, 376-377; 546/194, 197, 201, 196; 514/318, 320, 321, 323

[56] References Cited

U.S. PATENT DOCUMENTS

| | | | |
|---|---|---|---|
| 4,181,722 | 1/1980 | Beranger et al. | 544/376 |
| 4,563,458 | 1/1986 | Widding et al. | 544/376 |
| 4,659,737 | 4/1987 | Kabbe et al. | 544/376 |
| 4,803,203 | 2/1989 | Caprathe et al. | 544/376 |

FOREIGN PATENT DOCUMENTS 0114374  8/1984  European Pat. Off. .
0157267 10/1985  European Pat. Off. .

Primary Examiner—Glennon H. Hollrah
Assistant Examiner—James H. Turnipseed
Attorney, Agent, or Firm—Morgan & Finnegan

[57] ABSTRACT

New benzopyran derivatives of formula:

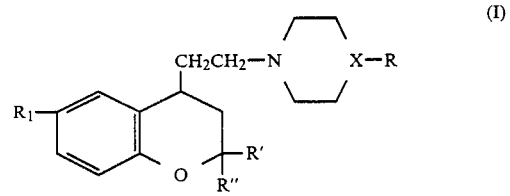

in which $R_1$ is hydrogen, halogen, hydroxy, alkoxy, nitro, amino, alkylsulphonamido, bis(alkylsulphonyl) amino or acylamino,
X is nitrogen or a >CH-radical
R is a radical of formula:

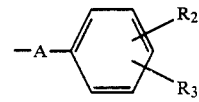

in which A denotes a single bond or methylene or, when X is nitrogen, A may denote carbonyl, and $R_2$ and $R_3$, which are identical or different, are hydrogen, halogen, hydroxy, alkyl, alkoxy, nitro, amino, alkylsulphonamido, bis(alkylsulphonyl)amino, acylamino, sulphamoyl or cyano, or, when they are adjacent, together form a methylenedioxy or ethylenedioxy radical, or else
R is pyridyl or 2(2H)-benzimidazolonyl if X denotes >CH—, and
R' and R" are identical and are hydrogen or alkyl, their isomeric forms and mixtures thereof, and their acid addition salts, can be used as antiarrhythmic and antifibrillation agents.

9 Claims, No Drawings

BENZOPYRAN DERIVATIVES AND PHARMACEUTICAL COMPOSITIONS CONTAINING THEM

This application is a continuation-in-part of application Ser. No. 222,613 filed July 21, 1988.

The present invention relates to benzopyran derivatives, their salts, their preparation and pharmaceutical compositions containing them.

German patent application 3,300,004 has described 4-aminomethylbenzopyran derivatives active as hypotensives and muscle relaxants, and corresponding to the formula:

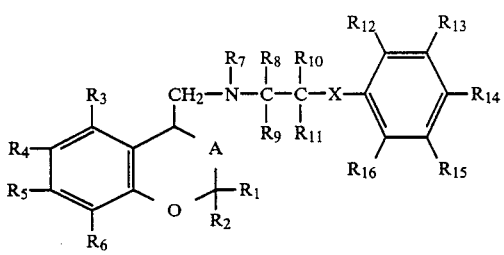

in which
A denotes particularly a single bond,
$R_1$, $R_2$, $R_8$, $R_9$, $R_{10}$ and $R_{11}$ may denote hydrogen atoms,
$R_3$, $R_4$, $R_5$ and $R_6$ may be hydrogen atoms or alkoxy radicals,
$R_{12}$ to $R_{16}$ may be, inter alia, hydrogen atoms or alkoxy radicals, or 2 of these radicals which are adjacent may form a methylenedioxy radical, and $-NR_7-CR_8R_9-CR_{10}R_{11}-X-$ may denote a piperazinyl radical.

It has now been found that the benzopyran derivatives of the formula

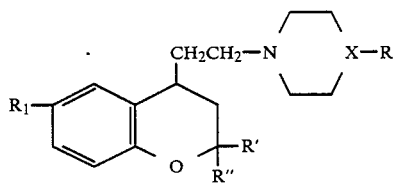 (I)

in which $R_1$ is hydrogen, halogen, hydroxy, alkoxy, nitro, amino or alkylsulphonamido, bis(alkylsulphonyl)amino, or acylamino, X denotes a nitrogen atom or a >CH— radical, R is a radical of formula:

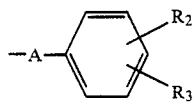 (II)

in which A is a single bond, methylene or, when X is a nitrogen atom, carbonyl, and $R_2$ and $R_3$, which are identical or different, are hydrogen, halogen, hydroxy, alkyl, alkoxy, nitro, amino, alkylsulphonamido, bis(alkylsulphonyl)amino, acylamino, sulphamoyl or cyano, or $R_2$ and $R_3$, when they are adjacent, together form a methylenedioxy or ethylenedioxy radical, or R is pyridyl or 2(2H)-benzimidazolonyl if X denotes >CH—, and R' and R", which are identical, are hydrogen or alkyl, and their salts, produce a particularly interesting increase in the refractory periods of heart muscle, which corresponds to the antifibrillation effects of the antiarrhythmic products of class III according to Vaughan Williams' classification.

In formula (I), when $R_1$ and $R_2$ and $R_3$ (in the symbol R) denote a halogen atom, the latter may be chosen from fluorine, chlorine, bromine or iodine; when $R_1$, $R_2$ or $R_3$ denote or contain alkyl or acyl radicals, the latter may be straight or branched and contain 1 to 4 carbon atoms.

It is to be understood that the products of general formula (I) exist in isomeric, i.e. enantiomeric, forms, and that these isomers and their mixtures are included within the scope of the present invention.

According to a feature of the invention, the products of general formula (I) may be obtained by reaction of a product of formula:

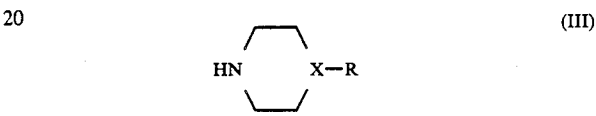 (III)

or a salt thereof, in which X and R are as hereinbefore defined, with a benzopyran derivative of formula:

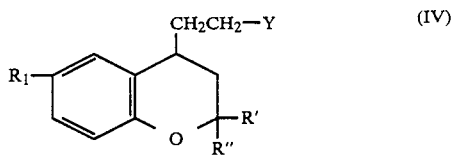 (IV)

in which $R_1$, R' and R" are defined as before and Y denotes a halogen atom or an alkylsulphonyloxy or arylsulphonyloxy radical.

The operation is advantageously carried out in the presence of an acid-scavenger. It is also possible to operate without an acid-scavenger, in the presence of 2 equivalents of the product of general formula (III).

When Y denotes a halogen atom, it may be chosen from chlorine or bromine atoms.

When Y denotes an alkylsulphonyloxy radical, it denotes particularly the methylsulphonyloxy radical and when it denotes an arylsulphonyloxy radical, it may be, inter alia, the p-toluenesulphonyloxy radical.

An alkali or alkaline-earth metal hydroxide (e.g. sodium hydroxide or potassium hydroxide), an alkali metal carbonate (e.g. sodium bicarbonate or potassium carbonate), or a nitrogenous organic base such as, e.g., triethylamine, is advantageously employed as an acid-scavenger.

The reaction is carried out in an inert solvent such as a ketone (e.g. acetone or butanone), an ether (e.g. tetrahydrofuran or dioxane), an alcohol (e.g. methanol or ethanol), a hydrocarbon (e.g. hexane or toluene), acetonitrile, dimethylformamide or dimethyl sulphoxide, or in a mixture of such solvents, at a temperature of between 20° C. and the reflux temperature of the reaction mixture.

It is to be understood that in the case where $R_1$, $R_2$ and/or $R_3$ (in R) denote an amino radical, the latter is protected beforehand. Similarly, when $R_2$ and/or $R_3$ denote a hydroxy radical, it is preferable to protect this radical before the reaction.

The protection is provided using any compatible group whose application and removal do not alter the remainder of the molecule. The operation is performed particularly according to the methods described by T. W. Greene, Protective Groups in Organic Synthesis, A. Wiley — Interscience Publishers (1981), or by McOmie, Protective Groups in Organic Chemistry, Plenum Press (1973).

According to the invention, the products of general formula (I) in which the radicals $R_1$, $R_2$ and/or $R_3$ denote a hydroxy radical may also be obtained from the corresponding product of general formula (I) in which the radical $R_1$, $R_2$ and/or $R_3$ to be converted denotes an alkoxy radical, by treatment in a concentrated acid medium.

The reaction is generally carried out by treatment with hydrobromic acid or a mixture of acids, for example by treatment with a hydrobromic acid-acetic acid mixture, at the reflux temperature of the reaction mixture.

According to the invention, the products of general formula (I) in which the symbols $R_1$, $R_2$ and/or $R_3$ denote an amino, alkylsulphonamido, bis(alkylsulphonyl)-amino or acylamino radical may also be obtained by catalytic hydrogenation in an acid medium of the benzopyran derivative of general formula (I), in which the radical $R_1$, $R_2$ and/or $R_3$ to be converted denotes a nitro radical, and then, when it is desired to obtain a product of general formula (I) in which $R_1$, $R_2$ and/or $R_3$ denote an alkylsulphonamido, bis(alkylsulphonyl)amino or acylamino radical, the amine derivative obtained is converted by sulphonylation or by acylation respectively.

The hydrogenation is advantageously carried out at a temperature of between 20° and 50° C., in an acid such as, e.g., acetic acid or hydrochloric acid, in an organic solvent such as an alcohol (e.g. methanol, ethanol or isopropanol), in a mixture of solvents, or in a hydroorganic medium (e.g. alcohol - water). It is also possible to operate directly in the acid, without supplementary addition of a solvent.

Palladium, platinum oxide or Raney nickel is generally employed as a catalyst.

If desired, the operation is performed under pressure.

The sulphonylation or the acylation is carried out by reaction of an activated form of an acid alkSO₃H or alk'COOH (alk and alk' being alkyl radicals) respectively, especially the acid halide (e.g. acid chloride) or the anhydride, and the operation is carried out in the presence of an acid-scavenger such as a nitrogenous organic base like a trialkylamine (e.g. triethylamine) or like pyridine, in an inert organic solvent such as a chlorinated solvent (e.g. dichloromethane or chloroform), an ether (e.g. ethyl ether or tetrahydrofuran) or in a mixture of these solvents, at a temperature of between −70° and +40° C.

If desired, the operation is carried out under nitrogen.

When it is desired to obtain the product of general formula (I) in which $R_1$, $R_2$ and/or $R_3$ denote a bis(alkylsulphonyl)amino radical, the operation is carried out in the presence of 2 equivalents of the corresponding sulphonic acid derivative.

According to the invention, the products of general formula (I) in which A denotes a carbonyl radical (when X is a nitrogen atom) may also be prepared by reaction of a benzoic acid of general formula:

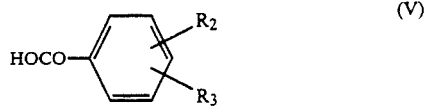

in which $R_2$ and $R_3$ are defined as before, or of a reactive derivative of this acid, with a benzopyran derivative of general formula:

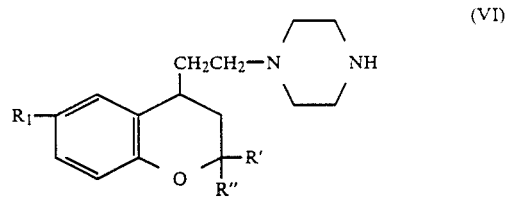

in which $R_1$, R' and R'' are defined as before.

It is to be understood that, when $R_1$, $R_2$ and/or $R_3$ denote amino or hydroxy radicals, the latter are protected before the reaction.

The protection and the removal of the protecting radicals are carried out in the conditions described above in the case of the process which consists in reacting the products of general formula (III) and (IV).

When the acid of general formula (V) is employed, the operation is carried out in the presence of a peptide condensation agent such as a carbodiimide (e.g. dicyclohexylcarbodiimide) or N,N'-carbonyldiimidazole, or 2-ethoxy-1-ethoxycarbonyl-1,2-dihydroquinoline, in an organic solvent such as an ether (tetrahydrofuran), an amide (dimethylformamide), a nitrile (acetonitrile) or a chlorinated solvent (e.g. dichloromethane), at a temperature of between −10° and +20° C.

When a reactive derivative of the acid of general formula (V) is used, then the reactant may be the anhydride, a mixed anhydride, an acid halide or an activated ester. The operation is then carried out either in an organic medium, optionally in the presence of an acid-scavenger such as a nitrogenous organic base (e.g. a trialkylamine or a pyridine) in a solvent such as mentioned above, or a mixture of these solvents at a temperature of between 0° and +20° C., or in a hydroorganic mixture in the presence of an alkaline condensation agent such as an alkali or alkaline-earth metal carbonate or bicarbonate, at a temperature of between 5° and 20° C.

The products of general formula (III) may be prepared according to the methods described by:
V. Nacci et al, Farmaco Ed. Sci., 328(5), 399 (1973),
P. C. Jain et al, J. Med. Chem., 10, 813 (1967),
J. Craig et al, Org. Synth., 5, 88 (1973),
Japanese patent application No. JA 82-093,962
Dutch patent application No. NE 65/10,107
U.S. Pat. No. 4,421,753
J. A. Kiritsy et al, J. Med. Chem., 21 (12), 1301 (1978)
D. Kohlbach, Arhiv. Hem. Farm. 11, 99 (1937) which are described below in the examples, or by analogy with these methods.

The products of general formula (IV) may be obtained by reaction of a halogenating agent or of an activated form of an alkylsulphonic or arylsulphonic acid with a 4-hydroxyalkylbenzopyran derivative of general formula:

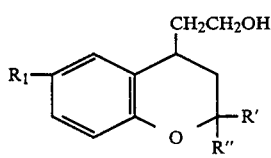 (VII)

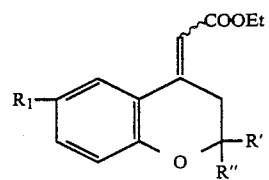 (IX)

in which $R_1$, R' and R" are defined as previously.

When it is desired to prepare a product of general formula (IV) in which Y is a halogen atom, the halogenating agents may be chosen from thionyl chloride or the halogen derivatives of phosphorus such as phosporus oxychloride or phosphorus tribromide. It is also possible to react allyl bromide in the presence of N,N'-carbonyldiimidazole.

When it is desired to prepare a product of general formula (IV) in which Y is alkylsulphonyloxy or arylsulphonyloxy, the anhydride or the halide of the corresponding acid is advantageously reacted.

The reaction is generally carried out in the presence of a nitrogenous organic base such as triethylamine or pyridine, in an organic solvent such as a chlorinated solvent (e.g. methylene chloride) or an ether (e.g. tetrahydrofuran or dioxane), the reaction being carried out a temperature between 0° C. and the reflux temperature of the reaction mixture.

The products of general formula (IV) in which $R_1$ is a nitro radical may be obtained by nitration of a derivative of general formula (IV) in which $R_1$ is a hydrogen atom.

The operation is advantageously carried out using a nitric acid - acetic acid mixture at a temperature of between 0° and 20° C.

The products of general formula (IV) in which $R_1$ is a hydroxy radical may also be obtained from a product of general formula (IV) in which $R_1$ is an alkoxy radical, by treatment in concentrated acid medium. The operation is carried out under the conditions described previously for the preparation of a product of general formula (I) in which $R_1$ denotes a hydroxy radical from the corresponding product in which $R_1$ is an alkoxy radical.

The 4-hydroxyalkylbenzopyran derivative of general formula (VII) may be prepared by reduction of the corresponding ester of general formula:

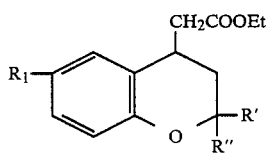 (VIII)

in which $R_1$, R' and R" are defined as previously.

The operation is generally carried out using lithium aluminium hydride in an organic solvent such as an ether (e.g. tetrahydrofuran) at a temperature of between 0° and 30° C.

The ester of general formula (VIII) may be obtained by reduction of the benzopyran derivative of general formula:

in which $R_1$, R' and R" are defined as previously.

The operation is carried out by catalytic hydrogenation in the presence of palladium, in an organic solvent such as an alcohol (e.g. methanol or ethanol), at a temperature of between 10° and 50° C.

The benzopyran derivative of general formula (IX) may be prepared by the Witting reaction, from a 4-chromanone derivative of general formula:

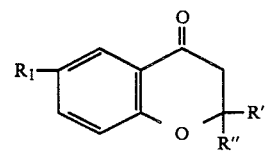 (X)

in which $R_1$, R' and R" are defined as previously.

The operation is advantageously carried out using ethyl diethylphosphonoacetate in the presence of sodium hydride, in an organic solvent such as an ether (e.g. tetrahydrofuran or dimethoxyethane) at a temperature between 0° C. and the reflux temperature of the reaction mixture.

The 4-chromanone derivative of general formula (X) in which $R_1$ is other than hydrogen may be prepared by application of the method described by Pfeiffer et al, Chem. Ber., 58 (1954), or according to the methods described by G. P. Ellis, Heterocyclic compounds, chromenes, chromanones and chromones, John Wiley and Sons (1977).

The 4-chromanone derivative of general formula (X) in which $R_1$ is a fluorine atom may be prepared according to the method described in French patent application no. 2,588,860.

The 4-chromanone derivatives of general formula (X) in which $R_1$ is an amino, alkylsulphonamido, bis(alkylsulphonyl)amino, trifluoromethylsulphonamido or acylamino radical may be obtained from the 4-chromanone derivative of general formula (X) in which $R_1$ is a nitro radical, by analogy with the methods described for the preparation of the products of general formula (I) in which the radical $R_1$ is defined as above.

2,2-Dimethyl-4-chromanone may be obtained according to the method described in Belgian Pat. No. 844,943.

The products of general formula (V) may be prepared according to, or by analogy with, the methods described in:
J. Am. Chem. Soc., 70, 4177 (1948), and
EP 023,578.

The benzopyran derivatives of general formula (VI) may be obtained by reaction of piperazine with a benzopyran derivative of general formula (IV).

The reaction is carried out under the conditions described previously for the reaction of the products of general formula (III) with the benzopyran derivatives of general formula (IV), in the presence of an excess of piperazine (2 equivalents), without supplementary addition of an acid-scavenger.

The enantiomers of the products according to the invention may be separated according to known methods.

The operation is carried out particularly by preparing the enantiomer of the hydroxyethylbenzopyran derivative of general formula (VII) which is converted into a product of general formula (I) according to the process described previously.

The optically active derivative of general formula (VII) is obtained by preparation of an optically active amide of general formula:

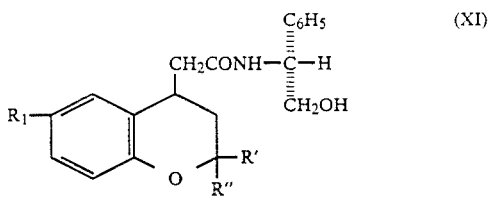

(XI)

in which $R_1$, $R'$ and $R''$ are defined as previously, separation of the isomers by chromatography, hydrolysis of the required isomer, and then reduction of the acid obtained.

The hydrolysis of the isomer of the product of general formula (XI) may be performed by any known method which does not alter the remainder of the molecule; the operation is advantageously carried out in an acid medium (acetic acid or hydrochloric acid mixtures) at the reflux temperature of the reaction mixture.

The reduction of the acid to alcohol is performed by the usual methods. In particular, diborane is employed as a reducing agent and the operation is advantageously carried out in an ether such as tetrahydrofuran at temperatures of between 0° and 30° C.

The product of general formula (XI) may be prepared from the acid of general formula:

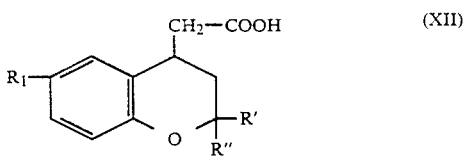

(XII)

in which $R_1$, $R'$ and $R''$ are defined as previously, by any known method for preparing an amide from an acid.

The operation is advantageously carried out using the acid chloride of the acid of general formula (XII) (which may be prepared in situ) in an inert organic solvent such as a chlorinated solvent (e.g. dichloromethane) in the presence of an acid-scavenger like a nitrogenous organic base (e.g. triethylamine), at a temperature of between 0° and 30° C.

The acid of general formula (XII) may be obtained from the corresponding ester by any known method for obtaining an acid from an ester without affecting the remainder of the molecule.

In particular, saponification of the ester of general formula (VIII) is performed using potassium hydroxide in methanol at the reflux temperature of the reaction mixture.

The acid chloride is prepared by treating the corresponding acid with thionyl chloride at the reflux temperature of the reaction mixture.

The new benzopyran derivatives according to the invention may be purified, where appropriate, by physical methods such as crystallization or chromatography.

The products according to the invention may be converted into addition salts with acids. The salt formed precipitates after an optional concentration of its solution, and it is separated off by filtration, decanting or freeze-drying. According to the process of the present invention, the products are generally obtained in hydrochloride form. These salts may be liberated and converted into salts of other acids according to the usual methods.

Examples of pharmaceutically acceptable salts which may be mentioned are addition salts with inorganic acids (hydrochlorides, hydrobromides, sulphates, nitrates or phosphates) or organic acids (succinates, fumarates, acetates, propionates, maleates, methanesulphonates, p-toluenesulphonates or isethionates) or substitution derivatives of these compounds.

The products according to the invention exhibit particularly interesting cardiac antiarrhythmic and antifibrillation properties, characteristic of Vaughan William's class III, reflected in a lengthening of the refractory periods.

In particular, on a guinea-pig papillary muscle in vitro, they produce an increase of between 5% and values greater than 50% in the period of the initial action potential, according to the technique for measuring a recording of the intracellular action potential described by E. Coraboeuf and S. Weidmann, C.R. Soc. Biol., 143, 1329 (1949).

Furthermore, the benzopyran derivatives according to the invention exhibit low toxicity. They have generally been found nontoxic in an oral dose of 300 mg/kg in the mouse.

The products of general formula (I) which are more especially interesting are those in which:

$R_1$ denotes a hydrogen, chlorine or fluorine atom or a hydroxy, methoxy, nitro, amino or methylsulphonylamino radical, X denotes a nitrogen atom or a >CH— radical, R denotes a radical of general formula (II) in which:

A is a single bond or a methylene radical or, when X is a nitrogen atom, A may also denote a carbonyl radical, and $R_2$ and $R_3$, which are identical or different, are situated in the 3 and/or 4 position and denote a hydrogen or fluorine atom or a hydroxy, methyl, methoxy, nitro, amino, methylsulphonamido, bis(methylsulphonyl)amino, acetylamino, sulphamoyl or cyano radical, or, when they are adjacent, form together a methylenedioxy or ethylenedioxy radical, or else R denotes a pyridyl radical or denotes a 2(2H)-benzimidazolonyl radical if X denotes >CH—, $R'$ and $R''$ are identical and denote hydrogen atoms or methyl radicals in their isomeric forms or their mixtures and particularly the following products:

1-[2-(3,4-dihydro-1(2H)-benzopyran-4-yl)ethyl]-4-(3,4-dimethoxyphenyl)piperidine, its isomeric forms and mixtures thereof, 1-[2-(6-amino-3,4-dihydro-1(2H)-benzopyran-4-yl)ethyl]-4-(3,4-dimethoxyphenyl)piperidine, its isomeric forms and mixtures thereof, 1-[2-(3,4-dihydro-1(2H)-benzopyran-4-yl)ethyl]-4-(4-methylsulphonamidophenyl)piperidine, its isomeric forms and mixtures thereof, 1-[2-(3,4-dihydro-1(2H)-benzopyran-4-yl)ethyl]-4-(4-methylsulphonamidophenyl)piperazine, its isomeric forms and mixtures thereof, and 1-{1-[2-(3,4-dihydro-1(2H)-benzopyran-4-yl)ethyl]-4-piperidinyl}-1,3-dihydro-2(2H)-benzimidazolone, its isomeric forms and mixtures thereof.

The following examples illustrate the present invention.

In the examples which follow, the chromatographic separations are carried out on silica gel (60–200 μ), unless stated otherwise.

EXAMPLE 1

4-[2-bromoethyl]-3,4-dihydro-2H-benzopyran (9.7 g), 1-(3,4-dimethoxyphenyl)piperazine dihydrochloride (11.12 g), dry potassium carbonate (15.6 g) and potassium iodide (6.8 g) are heated under reflux in 2-butanone (300 cc) for 3 hours.

The reaction mixture is filtered through sintered glass and the solvent is then evaporated off under reduced pressure (5.2 kPa). The oil obtained is extracted with dichloromethane (300 cc) and is then washed with a 1N sodium hydroxide solution (40 cc), is washed with water, and then the organic phase is dried over magnesium sulphate.

After evaporation, the oil obtained is taken up with ethanol (100 cc) and a 2N solution of hydrochloric acid in ethanol (35 cc) is added. After the precipitate formed has been filtered off, on sintered glass, 1-[2-(3,4-dihydro-1(2H)-benzopyran-4-yl)ethyl]-4-(3,4-dimethoxyphenyl)piperazine dihydrochloride (14 g) is obtained in the form of a white solid melting with decomposition in the region of 226° C.

1-(3,4-dimethoxyphenyl)piperazine may be prepared according to the method described by P.C. Jain et al, J. Med. Chem., 10, 813 (1967).

2-Bromo-4-ethyl-3,4-dihydro-2H-benzopyran may be prepared as follows:

2-(3,4-Dihydro-1(2H)-benzopyran-4-yl)ethanol (13.8 g) is added with stirring to acetonitrile (115 cc), followed by allyl bromide (91.2 g) and, lastly, N,N'-carbonyldiimidazole (12.6 g).

The mixture is stirred for 3 hours 10 minutes at approximately 20° C. and then for 2 hours under reflux.

The reaction mixture is then concentrated under reduced pressure (5.2 kPa) and the residue obtained is chromatographed on a column 5.5 cm in diameter, containing silica gel (200 g), using dichloromethane (550 cc) as eluent and collecting 100-cc fractions. The fractions between 350 and 550 cc are concentrated to dryness.

4-(2-Bromoethyl)-3,4-dihydro-2H-benzopyran (17.7 g) is thus obtained in the form of a light brown oil.

Proton NMR spectrum (250 MHz, CDCl$_3$, β in ppm): 6.8 to 7.2 (mt, aromatic 4H), 4.21 (mt, —O—CH$_2$—), 3.55 (mt, —CH$_2$—Br), 3.08 (mt, >CH—), 1.92 and 2.92 (mt, —CH$_2$— at -3), 2.08 and 2.34 (mt, —CH$_2$CH$_2$Br).

2-(3,4-Dihydro-1(2H)-benzopyran-4-yl)ethanol may be prepared as follows:

Tetrahydrofuran (500 cc) is added to lithium aluminium hydride (5.96 g) and is cooled to 0° C. Ethyl 2-(3,4-dihydro-1(2H)-benzopyran-4-yl)ethanoate (17.25 g) in tetrahydrofuran (60 cc) is then added with stirring.

After 1 hour's stirring at 20° C., hydrolysis is carried out with stirring by adding sodium sulphate hydrate (10 H$_2$O) until precipitation, and the reaction mixture is then left to stand for 15 hours.

After filtration of the precipitate formed and evaporation of the solvent under reduced pressure, 2-(3,4-dihydro-1(2H)-benzopyran-4-yl)ethanol (13.8 g) is isolated in the form of a brown oil.

NMR spectrum (250 MHz, CDCl$_3$, δ in ppm): 6.8 to 7.2 (mt, aromatic 4H), 4.22 (mt, —O—CH$_2$—), 3.83 (mt, —CH$_2$—OH), 3.04 (mt, >CH—), 1.83 and 2.90 (mt, —CH$_2$— at -3 and —CH$_2$—CH$_2$OH), 1.62 (s, —OH).

Ethyl (3,4-dihydro-1(2H)-benzopyran-4-yl)ethanoate can be prepared as follows:

Ethyl (E,Z)(3,4-dihydro-1(2H)-benzopyran-4-ylidene)acetate (50.6 g) in methanol (1 litre) is hydrogenated at 20° C. at atmospheric pressure, in the presence of 10% palladium on charcoal (5.06 g).

After filtration through kieselguhr and concentration to dryness under reduced pressure (5.2 kPa), ethyl (3,4-dihydro-1(2H)-benzopyran-4-yl)ethanoate (48.8 g) is obtained in the form of a pale yellow oil.

NMR spectrum (250 MHz, CDCl$_3$, δ in ppm): 6.75 to 7.2 (mt, aromatic 4H), 4.98 (q +mt, —O—CH$_2$—+—CO—OCH$_2$—CH$_3$), 3.37 (mt, >CH—), 2.53 and 2.82 (dd, —CH$_2$—CO—), 1.87 and 2.18 (mt, —CH$_2$— at -3), 1.30 (t, —COO—CH$_2$—CH$_3$).

Ethyl (E,Z) (3,4-dihydro-1(2H)-benzopyran-4-ylidene) acetate may be prepared as follows:

Sodium hydride (80%, 20.4 g) is added with stirring to anhydrous tetrahydrofuran (1 litre), followed, in small portions, by ethyl diethylphosphonoacetate (153 g), while the temperature of the reaction mixture is kept in the region of 20° C. 4-Chromanone (45 g) in anhydrous tetrahydrofuran (100 cc) is then added to the light yellow solution thus obtained, while the temperature is kept below 0° C. After 22 hours at 20° C., the reaction mixture is concentrated under reduced pressure and then the oil obtained is extracted with dichloromethane (2×700 cc). The organic phase is washed with water and is then dried over magnesium sulphate and concentrated to dryness under reduced pressure. The evaporation residue is chromatographed on a column 9 cm in diameter, containing silica gel (1.6 kg), using a cyclohexane-ethyl acetate mixture (90–10 by volume, 6.3 litres) as eluent and collecting 250-cc fractions. The fractions between 2.8 l and 6.3 l are concentrated to dryness.

A mixture of E and Z isomers of ethyl (3,4-dihydro-1(2H)-benzopyran-4-ylidene)acetate (50.6 g) is thus obtained in the form of a pale yellow oil.

NMR spectrum (400 MHz, CDCl$_3$, δ in ppm):

E isomer (75%): 6.8 to 7.61 (mt, aromatic 4H), 6.36 (s, =CH—CO—), 4.23 (mt, —O—CH$_2$—), 4.23 (mt, —CO—OCH$_2$—CH$_3$), 3.41 (mt, —CH$_2$— at -3), 1.32 (mt, —CO—OCH$_2$—CH$_3$), Z isomer (25%): 6.8 to 7.83 (mt, aromatic 4H), 5.61 (s, =CH—CO—), 4.38 (t, —O—CH$_2$—), 4.23 (mt, —CO—OCH$_2$—CH$_3$), 2.65 (t, —CH$_2$— at -3), 1.32 (mt, —CO—OCH$_2$—CH$_3$).

EXAMPLE 2

The A isomer of 1-[2-(3,4-dihydro-1(2H)-benzopyran-4-yl)ethyl]-4-(3,4-dimethoxyphenyl)piperazine dihydrochloride is prepared by following the procedure of Example 1 but starting with the A isomer of 4-(2-bromoethyl -3,4-dihydro-(2H)-benzopyran (0.86 g), 1-(3,4-dimethoxyphenyl)piperazine dihydrochloride (1.10 g) and then dry potassium carbonate (1.38 g) and potassium iodide (0.6 g) in 2-butanone (15 cc).

The oil obtained is taken up with ethanol (9 cc) and a 5N solution of hydrochloric acid in isopropanol (1.5 cc)

is added. The precipitate thus obtained is filtered off and then crystallized from methanol (150 cc).

The A isomer of 1-[2-(3,4-dihydro-1(2H)-benzopyran-4-yl)ethyl]-4-(3,4-dimethoxyphenyl)piperazine dihydrochloride (1.28 g) is thus obtained in the form of a white solid melting with decomposition in the region of 219°-221° C.

$[\alpha]_D^{20} = -13° \pm 0.8$ (c=0.736, H$_2$O).

The A isomer of 4-(2-bromoethyl)-3,4-dihydro(2H)-benzopyran may be prepared by following the procedure of Example 1 but starting from the A isomer of 2-(3,4-dihydro-1(2H)-benzopyran-4-yl)ethanol (0.96 g), from allyl bromide (4.9 g) and from N,N'-carbonyldiimidazole (0.875 g) in acetonitrile (8 cc). The residue obtained is chromatographed on a column 2 cm in diameter, containing silica gel (25 g), using dichloromethane (120 cc) as eluent and collecting 30-cc fractions. The fractions between 60 and 120 cc are concentrated to dryness.

The A isomer of 4-(2-bromoethyl)-3,4-dihydro-(2H)-benzopyran (0.86 g) is thus obtained in the form of a colourless oil which is used as such in the following step.

The A isomer of 2-(3,4-dihydro-1(2H)-benzopyran-4-yl)ethanol may be prepared in the following manner: Anhydrous tetrahydrofuran (5 cc) is added to the A isomer of (3,4-dihydro-1(2H)-1-benzopyran-4-yl)ethanoic acid (1.26 g) and cooled to 0° C. A 1M solution of diborane in tetrahydrofuran (17.5 cc) is then slowly added with stirring. After the end of the addition the temperature of the reaction mixture is allowed to return to 20° C. and the mixture is kept there with stirring for 4 hours 30, and methanol (10 cc) is then added to the reaction mixture. The oil obtained after removal of the solvent is chromatographed on a column 2 cm in diameter, containing silica gel (60 g), using a dichloromethane-acetone mixture (80-20 by volume, 210 cc) as eluent and collecting 30-cc fractions. The fractions between 150 and 210 cc are concentrated to dryness.

The A isomer of 2-(3,4-dihydro-1(2H)-benzopyran-4-yl)ethanol (1.07 g) is thus obtained in the form of a colourless oil which is used as such in the following step.

The A isomer of (3,4-dihydro-1(2H)-benzopyran-4-yl)ethanoic acid may be prepared in the following manner:

Concentrated hydrochloric acid (10 cc) is added to the A isomer of N-(2-hydroxy-1-phenylethyl)-(3,4-dihydro-1(2H)-benzopyran-4-yl)ethanamide (3 g) in pure acetic acid (10 cc) and is heated under reflux for 1 hour 30. The reaction mixture is concentrated to dryness under reduced pressure (5.2 kPa) and is then extracted with ethyl ether. The ether phase is washed with water and concentrated to dryness under reduced pressure, and the residue obtained is taken up with a 1N sodium hydroxide solution (110 cc) and then extracted with dichloromethane (200 cc).

The alkaline liquor is acidified with concentrated hydrochloric acid (12 cc), and then extracted with dichloromethane. The organic phase is then washed with water and dried over magnesium sulphate. The residue obtained after concentration to dryness is crystallized in an isopropyl acetate-petroleum ether (40°-60° C.) mixture and yields the A isomer of (3,4-dihydro-1(2H)-benzopyran-4-yl)ethanoic acid (1.95 g) in the form of cream-coloured crystals melting at 77°-78° C.

$[\alpha]_D^{20} = -18.5° \pm 0.5$ (c=1.136, ethanol).

The A isomer of N-(2-hydroxy-1-phenylethyl)-(3,4-dihydro-1(2H)-benzopyran-4-yl)ethanamide may be prepared by proceeding in the following manner:

Triethylamine (3.9 cc) is added to (R)-(−)-2-amino-2-phenylethanol (3.45 g) in dichloromethane (25 cc) and cooled to 5° C. and then a solution of (3,4-dihydro-1(2H)-benzopyran-4-yl)ethanoyl chloride (5.3 g) in dichloromethane (10 cc) is introduced dropwise. The temperature of the reaction mixture is kept at 0° C. for 4 hours and the reaction mixture is then left to stand, with stirring, for 15 hours at 20° C. After washing the organic phase with a 1N solution of hydrochloric acid and then with a 1N solution of sodium hydroxide, the chloromethylenic solution is washed with water and then dried over magnesium sulphate.

After filtration and concentration to dryness under reduced pressure (5.2 kPa), a residue is obtained which consists of a mixture of diastereo isomers, which is then chromatographed on a column 9 cm in diameter, containing silica gel (32–63 μ, 1 kg), using a dichloromethane-ethanol mixture (95-5 by volume, 8.4 liters) as eluent and collecting 125-cc fractions. The fractions between 4 l and 5 l concentrated to dryness yield the A isomer of N-(2-hydroxy-1-phenylethyl)-(3,4-dihydro-1(2H)-benzopyran-4-yl)ethanamide (3.2 g) in the form of white crystals melting at 143° C.

$[\alpha]_D^{20} = -43.9° \pm 0.5$ (c=1.504, ethanol).

(3,4-Dihydro-1(2H)-benzopyran-4-yl)ethanoyl chloride may be prepared in the following manner:

(3,4-Dihydro-1(2H)-benzopyran-4-yl)ethanoic acid (5 g) is heated in thionyl chloride (12 cc) under reflux for 6 hours.

After distillation, (3,4-dihydro-1(2H)-benzopyran-4-yl)ethanoic acid (4.1 g) is obtained in the form of a yellow oil, the boiling point of which is 110°-120° C. at 2.63 Pa.

(3,4-Dihydro-1(2H)-benzopyran-4-yl)ethanoic acid may be prepared in the following manner:

Ethyl (3,4-dihydro-1(2H)-benzopyran-4-yl)ethanoate (15 g) and potassium hydroxide pellets (23.5 g) in methanol (250 cc) are heated under reflux for 2 hours 15.

The reaction mixture is concentrated under reduced pressure (5.2 kPa), and is taken up with water and then extracted with ethyl ether (300 cc). The aqueous phase is then acidified with a concentrated hydrochloric acid solution (45 cc) and then extracted with dichloromethane (600 cc). The organic phase is then washed with water and then dried over magnesium sulphate. The residue obtained after concentration to dryness is recrystallized from an isopropyl acetate-petroleum ether (40°-60°) mixture (50-50 by volume, and yields (3,4-dihydro-1(2H)-benzopyran-4-yl)ethanoic acid (9 g) in the form of white crystals melting at 90° C.

EXAMPLE 3

The B isomer of 1-[2-(3,4-dihydro-1(2H)benzopyran-4-yl)ethyl]-4-(3,4-dimethoxyphenyl)piperazine dihydrochloride may be prepared by following the procedure of Example 2 but starting with the B isomer of 4-[1-(2-bromoethyl)]-3,4-dihydro-(2H)-benzopyran (0.72 g), 1-(3,4-dimethoxyphenyl)piperazine dihydrochloride (0.92 g) and then dry potassium carbonate (1.38 g) and potassium iodide (0.51 g) in 2-butanone (15 cc). The B isomer of 1-[2-(3,4-dihydro-1(2H)-benzopyran-4-yl)ethyl]-4-(3,4-dimethoxyphenyl)piperazine dihydrochloride (0.80 g) is obtained in the form of a white solid melting with decomposition in the region of 219°-220° C.

$[\alpha]_D^{20} = +12.4 \pm 0.6°$ (c=0.840, water).

The B isomer of 4-[1-(2-bromoethyl)]-3,4-dihydro-(2H)-benzopyran may be prepared by following the procedure of Example 2 but starting with the B isomer of 2-(3,4-dihydro-1(2H)-benzopyran-4-yl)ethanol (0.76 g), allyl bromide (3.88 g) and N,N'-carbonyldiimidazole (0.69 g) in acetonitrile (6.4 cc). After purification as described in Example 2, the B isomer of 4-[1-(2-bromoethyl)]-3,4-dihydro-(2H)-benzopyran (0.72 g) is obtained in the form of a pale yellow oil.

The B isomer of 2-(3,4-dihydro-1(2H)-benzopyran-4-yl)ethanol may be prepared by following the procedure of Example 2 but starting with the B isomer of (3,4-dihydro-1(2H)-benzopyran-4-yl)ethanoic acid (0.90 g) in tetrahydrofuran (4 cc) and a 1M solution of diborane in tetrahydrofuran (12.6 cc). 2-(3,4-Dihydro-1(2H)-benzopyran-4-yl)ethanol (0.76 g) is thus obtained in the form of a colourless oil.

The B isomer of (3,4-dihydro-1(2H)-benzopyran-4-yl)ethanoic acid may be prepared by following the procedure of Example 2 but starting with the B isomer of N-2-(1-hydroxy-2-phenylethyl)(3,4-dihydro-1(2H)-benzopyran-4-yl)ethanamide (3 g) in pure acetic acid (10 cc) containing concentrated hydrochloric acid (10 cc). The B isomer of (3,4-dihydro-1(2H)-benzopyran-4-yl)ethanoic acid (0.96 g) is thus obtained in the form of cream-coloured crystals melting at 77°–78° C.

$[\alpha]_D^{20} = +17.4° \pm 0.5°$ (c=1.046, ethanol).

The B isomer of N-2-(1-hydroxy-2-phenylethyl)(3,4-dihydro-1(2H)-benzopyran-4-yl)ethanamide may be prepared by following the procedure of Example 2 but collecting the chromatography fractions between 6 liters and 8.4 liters. After concentration to dryness under reduced pressure (5.2 kPa), N-2-(1-hydroxy-2-phenylethyl)(3,4-dihydro-1(2H)-benzopyran-4-yl)ethanamide (3.05 g) is obtained in the form of white crystals melting at 140° C.

$[\alpha]_D^{20} = -6.5° \pm 0.3°$ (c=1.498, ethanol).

EXAMPLE 4

The procedure of Example 1 is followed starting with 4-(2-bromoethyl)-3,4-dihydro-(2H)-benzopyran (1.5 g), 1-phenylpiperazine (1.03 g) and then dry potassium carbonate (0.8 g) and potassium iodide (0.1 g) in 2-butanone (50 cc).

The oil is taken up with ethanol (30 cc) and a 2N solution of hydrochloric acid in ethanol (5 cc) is added.

1-[2-(3,4-dihydro-1(2H)-benzopyran-4-yl)ethyl]4-phenylpiperazine dihydrochloride (1.4 g) is thus obtained in the form of a white solid melting at 206° C.

EXAMPLE 5

The procedure of Example 1 is followed, starting with 4-(2-bromoethyl)-3,4-dihydro-(2H)-benzopyran (1 g), 4-phenylpiperidine (0.63 g), dry potassium carbonate (0.54 g) and then potassium iodide (0.7 g) in 2-butanone (50 cc).

The oil obtained is taken up with ethanol (10 cc) and a 2N solution of hydrochloric acid in ethanol (1.8 cc) is added.

After addition of ethyl ether (50 cc) followed by filtration of the precipitate formed, 1-[2-(3,4-dihydro-1(2H)-benzopyran-4-yl)ethyl]-4-phenylpiperidine hydrochloride (1.05 g) is obtained in the form of a white solid melting at 250° C.

EXAMPLE 6

The procedure of Example 1 is followed, starting with 4-(2-bromoethyl)-3,4-dihydro-(2H)-benzopyran (3.35 g), 4-(4-fluorophenyl)piperidine (3 g) and dry potassium carbonate (3.8 g) and then potassium iodide (2.31 g) in 2-butanone (115 cc).

The residue obtained is purified by chromatography on a column 5.5 cm in diameter, containing silica gel (300 g), using a dichloromethane-acetone mixture (75-25 by volume) as eluent and collecting 250-cc fractions. The fractions between 1,000 and 3,000 cc are concentrated to dryness. The oil obtained is taken up with ethanol (16 cc) and then a 5N solution of hydrochloric acid in isopropanol (3 cc) is added.

The mixture is concentrated to dryness and recrystallized from 2-butanone (10 cc). 1-[2-(3,4-Dihydro-1(2H)-benzopyran-4-yl)ethyl]-4-(4-fluorophenyl)piperazine hydrochloride (2.05 g) is thus obtained in the form of white crystals melting in the region of 190° C. with decomposition.

4-(4-Fluorophenyl)piperidine hydrochloride may be prepared according to the method described in patent application No. NE 65/10,107.

EXAMPLE 7

The procedure of Example 1 is followed, but starting with 4-(2-bromoethyl)-3,4dihydro-(2H)-benzopyran (2 g), 1-(3-methoxyphenyl)piperazine hydrochloride (1.96 g) and dry potassium carbonate (2.28 g), followed by potassium iodide (1.3 g) in 2-butanone (70 cc). The residue obtained is filtered through a column 4.4 cm in diameter, containing silica gel (100 g), eluting with ethyl acetate (450 cc) and collecting 30-cc fractions. The fractions between 210 and 450 cc are concentrated to dryness. The oil obtained is taken up with ethanol (40 cc) and a 5N solution of hydrochloric acid in isopropanol (3.1 cc) is added.

1-[2-(3,4-Dihydro)-1(2H)-benzopyran-4-yl)ethyl]-4-(3-methoxyphenyl)piperazine dihydrochloride (2.4 g) is thus obtained in the form of a solid melting at 190° C.

EXAMPLE 8

The procedure of Example 1 is followed, starting with 4-(2-bromoethyl)-3,4-dihydro-(2H)-benzopyran (7 g), 1-(4-methoxyphenyl)piperazine hydrochloride (7.08 g) and dry potassium carbonate (6 g), followed by potassium iodide (4.81 g) in 2-butanone (230 cc). The base obtained is purified by chromatography on a column 6 cm in diameter, containing silica gel (300 g), eluting with a dichloromethane-acetone mixture (80-20 by volume) and collecting 250-cc fractions. The fractions between 750 cc and 2,500 cc are concentrated to dryness. The oil obtained is taken up with an acetone-ethanol mixture (60-40 by volume, 400 cc) and a 2N aqueous solution of hydrochloric acid (24.7 cc) is added. The precipitate formed is recrystallized from ethanol (200 cc). 1-[4-(3,4-Dihydro-1(2H)-benzopyranyl)ethyl]-4-(4-methoxyphenyl)piperazine dihydrochloride (8.3 g) is thus obtained in the form of a white solid, the melting point of which is 175° C.

EXAMPLE 9

The procedure of Example 1 is followed, but starting with 4-(2-bromoethyl)-3,4-dihydro-(2H)-benzopyran (5 g), 1-(4-nitrophenyl)piperazine (4.3 g) and from dry potassium carbonate (1.43 g), followed by potassium iodide (3.43 g) in 2-butanone (200 cc). The residue obtained is chromatographed on a column 4.4 cm in diameter, containing silica gel (100 g), using a dichloromethane-ethyl acetate mixture (50-50 by volume) as eluent, and collecting 20-cc fractions. The fractions between 100 and 300 cc are concentrated to dryness. The residue obtained is crystallized from isopropyl acetate (30 cc). 1-[2-(3,4-Dihydro-1(2H)-benzopyran-4-yl)ethyl]-4-(4-nitrophenyl)-piperazine (3.48 g) is thus obtained in the form of a yellow solid melting at 110° C.

EXAMPLE 10

The procedure of Example 1 is followed, but starting with 4-(2-bromoethyl)-3,4-dihydro-(2H)-benzopyran (5.85 g), 4-(4-nitrophenyl)piperidine (5.9 g) and dry potassium carbonate (6.6 g), followed by potassium iodide (4 g) in 2-butanone (200 cc).

The residue obtained is purified by chromatography on a column 4.4 cm in diameter, containing silica gel (100 g), using a dichloromethane-acetone mixture (50-50 by volume) as eluent and collecting 20-cc fractions. The fractions between 200 and 380 cc are concentrated to dryness.

After crystallization from isopropyl acetate (35 cc), 1-[2-(3,4-dihydro-1(2H)-benzopyran-4-yl)-ethyl]-4-(4-nitrophenyl)piperidine (4.25 g) is obtained in the form of a white solid melting at 100° C.

EXAMPLE 11

4-(2-Bromoethyl)-3,4-dihydro-(2H)-benzopyran (5 g),4-(piperazin-1-yl)benzenesulphonamide hydrobromide (6.4 g), dry potassium carbonate (5.53 g) and potassium iodide (3.32 g) in 2-butanone (100 cc) are heated under reflux for 7 hours 30 minutes.

The insoluble fraction is filtered off and washed twice with 2-butanone (50 cc), and is then taken up with distilled water (200 cc) and a concentrated hydrochloric acid solution (35%, 3.4 cc) in order to obtain a pH of 7. The product is filtered off again and the insoluble residue is washed with ethanol (50 cc and then twice with 20 cc). A grey powder (6.7 g) is obtained which is recrystallized from boiling 2-methoxyethanol (120 cc). After 2 hours' standing at 20° C., the crystals are filtered off and washed with ethanol (2×20 cc), with acetone (2×20 cc) and then with ethyl ether (2×20 cc) in order to obtain a white powder (3.54 g) which is recrystallized from 2-methoxyethanol (70 cc). After leaving to stand for 1 hour 30 minutes at 20° C., the crystals are filtered off and washed successively with 2-methoxyethanol (2×10 cc), ethanol (2×10 cc), acetone (2×10 cc) and finally ethyl ether (2×10 cc). 4-{1-[2-(3,4-Dihydro-1(2H)-benzopyran-4-yl)-1-ethyl]4-piperazinyl}benzenesulphonamide (2.47 g) is thus obtained in the form of a white solid melting at 225° C.

4-(piperazin-1-yl)benzenesulphonamide hydrobromide may be prepared according to the method of D. Kohlbach, Arhiv. Hem. Farm., 11, 99 (1937).

EXAMPLE 12

The procedure of Example 1 is followed, starting with 4-(2-bromoethyl)-3,4-dihydro-(2H)-benzopyran (15 g), 1-(4-cyanophenyl)piperazine (11.24 g), and dry potassium carbonate (8.3 g), followed by potassium iodide (9.95 g) in 2-butanone (200 cc). The mixture is heated under reflux for 7 hours. The oil obtained is taken up with distilled water (100 cc), extracted with dichloromethane (3×100 cc) and then the organic phase is dried over magnesium sulphate. Evaporation of the dichloromethane yields an oil (24 g). This oil is taken up with an isopropyl acetate - isopropyl ether mixture (50-50 by volume, 100 cc). After leaving to stand for 16 hours at 10° C., a solid (0.3 g) is removed. The filtrate is diluted with isopropyl ether (50 cc). After standing (1 hour at 10° C.), a cream-coloured solid (17.9 g) is obtained. This solid is recrystallized from an isopropyl acetate-isopropyl ether mixture (60-40 by volume, 100 cc). After standing (1 hour at 20° C.), 1-(4-cyanophenyl)-4-[2-(3,4-dihyddro-1(2H)-benzopyran-4-yl)ethyl]piperazine (1.55 g) is obtained in the form of a white solid melting at 106° C.

The 1-(4-cyanophenyl) piperazine may be prepared according to the method of J. A. Kiritsy and D. K. Yung, J. Med. Chem., 21 (12), 1301 (1978).

EXAMPLE 13

The procedure of Example 1 is followed, starting 4-(2-bromoethyl)-3,4-dihydro(2H)-benzopyran (2 g), 1-(3,5-dimethoxyphenyl)piperazine (1.84 g) and dry potassium carbonate (0.56 g), followed by potassium iodide (1.4 g) in 2-butanone (70 cc). The residue obtained is chromatographed on a column 4.4 cm in diameter, containing silica gel (100 g), using a dichloromethane-ethyl acetate mixture (50-50 by volume) as eluent and collecting 20-cc fractions. The fractions between 200 and 400 cc are concentrated to dryness. The oil obtained is taken up with ethanol (30 cc) and a 5N solution of hydrochloric acid in isopropanol (1.8 cc) is added. The crystals formed are filtered off and 1-[2-(3,4-dihydro-1(2H)-benzopyran-4-yl)ethyl]-4-(3,5-dimethoxyphenyl)piperazine dihydrochloride (1.9 g) is thus obtained in the form of a solid melting at 208° C.

EXAMPLE 14

The procedure of Example 1 is followed, starting with 4-(2-bromoethyl)-6-methoxy-3,4-dihydro-(2H)-benzopyran (0.72 g), 1-(3,4-dimethoxyphenyl)piperazine dihydrochloride (0.79 g) and dry potassium carbonate (1.1 g), followed by potassium iodide (0.05 g) in 2-butanone (30 cc).

The oil obtained is taken up with ethanol (20 cc) and a 2N solution of hydrochloric acid in ethanol (2.5 cc) is added.

1-[2-(6-Methoxy-3,4-dihydro-1(2H)-benzopyran-4-yl)-ethyl]-4-(3,4-dimethoxyphenyl)piperazine dihydrochloride (0.8 g) is obtained in the form of a white solid melting at 185° C.

4-(2-Bromoethyl)-6-methoxy-3,4-dihydro-(2H)-benzopyran may be prepared by following the procedure of Example 1 but starting with 2-(6-methoxy-3,4-dihydro-1(2H)-benzopyran-4-yl)ethanol (0.72 g), N,N'-carbonyldiimidazole (0.56 g) and allyl bromide (3 cc) in acetonitrile (20 cc). The oil thus obtained is chromatographed on a column 4.4 cm in diameter, containing silica gel (60 g), using dichloromethane (120 cc) as eluent and collecting 30-cc fractions. The fractions between 90 and 120 cc are concentrated to dryness.

4-(2-Bromoethyl)-6-methoxy-3,4-dihydro-(2H)-benzopyran (0.72 g) is thus obtained in the form of a pale yellow oil.

NMR spectrum (90 MHz, CDCL$_3$, δ in ppm): 6.6 to 6.8 (mt, aromatic 3H), 4.15 (mt, —O—CH$_2$—), 3.75 (s, —O—CH$_3$), 3.55 (mt, —CH$_2$—Br), 3.05 (mt, >CH—), 1.5 and 2.6 (mt, —CH$_2$— at -3 and —CH$_2$CH$_2$Br), 2-(6-Methoxy-3,4-dihydro-1(2H)-benzopyran-4-yl)ethanol may be prepared by following the procedure of Example 1 but starting with lithium aluminium hydride (0.29 g) and ethyl (6-methoxy-3,4-dihydro-1(2H)-benzopyran-4-yl)ethanoate (0.94 g) in tetrahydrofuran (50 cc). 2-(6-Methoxy-3,4-dihydro-1(2H)-benzopyran-4-yl)ethanol (0.72 g) is thus obtained in the form of a colourless oil.

NMR spectrum (90 MHz, CDCL₃, δ in ppm): 6.6 to 6.8 (mt, aromatic 3H), 4.15 (mt, —O—CH₂—), 3.85 (mt, —CH₂—OH), 3.75 (s, —O—CH₃), 2.85 -3.10 (mt, >CH—), 1.55-2.3 (mt, —CH₂— at -3 and —CH₂CH₂OH), 1.45 (s, —O—H), Ethyl (6-methoxy-3,4-dihydro-1(2H)-benzopyran-4-yl)-ethanoate may be prepared by following the procedure of Example 1, but starting with a mixture of (E,Z) ethyl methoxy-3,4-dihydro-1(2H)-benzopyran-4-ylideneacetate (1 g), and palladium on charcoal (0.2 g, 10%) in methanol (100 cc).

Ethyl (6-methoxy-3,4-dihydro-1(2H)-benzopyran-4yl)ethanoate (0.96 g) is thus obtained in the form of a pale yellow oil.

NMR spectrum (250 MHz, CDCl₃, δ in ppm): 6.65 to 6.8 (mt, aromatic 4H), 4.26 and 4.20 (mt+q, —O—CH₂—+—CO—OCH₂—CH₃), 3.76 (s, —O—CH₃), 3.36 (mt, >CH—), 2.53 and 2.81 (dd, —CH₂—CO₂—), 2.13 and 1.83 (mt, —CH₂—at 3), 1.3 (t, —CH₂—CH₃).

(E,Z)Ethyl 6-methoxy-3,4-dihydro-1(2H)-benzopyran-4-ylideneacetate may be prepared by following the procedure of Example 1 but starting with ethyl diethylphosphonoacetate (18.87 g), sodium hydride (2.52 g) and 6-methoxy-4-chromanone (5 g) [prepared according to Pfeiffer et al., Chem. Ber. 58 (1954)] in tetrahydrofuran (190 cc).

The oil obtained is chromatographed on a column 6.5 cm in diameter, containing silica gel (500 g), using a cyclohexane-ethyl acetate mixture (90-10 by volume, 3 liters) as eluent and collecting 250-cc fractions. The fractions between 1.9 liters and 2.4 liters are concentrated to dryness.

A mixture of E and Z isomers of ethyl 6-methoxy-3,4-dihydro-1(2H)-benzopyran-4-ylideneacetate (5.52 g) is thus obtained in the form of a pale yellow oil.

EXAMPLE 15

The procedure of Example 1 is followed, but starting with 4-(2-bromoethyl)-3,4-dihydro-(2H)-benzopyran (1.5 g) and 4-(3,4-dimethoxyphenyl) piperidine (1.5 g), followed by dry potassium carbonate (1.61 g) and potassium iodide (1 g) in 2-butanone (50 cc).

The oil obtained is taken up with ethanol (15 cc) and a 2N solution of hydrochloric acid in ethanol (2.7 cc) is added.

1-[2-(3,4-Dihydro-1(2H)-benzopyran-4-yl)ethyl]-4-(3,4-dimethoxyphenyl)piperidine hydrochloride (1.6 g) is thus obtained in the form of a white solid melting at 237° C.

4-(3,4-dimethoxyphenyl) piperidine may be prepared according to the method described by V. Nacci et al., Farmaco Ed. Sci., 328(5), 399–410 (1973).

EXAMPLE 16

The procedure of Example 2 is followed, but starting with the A isomer of 4-(2-bromoethyl)-3,4-dihydro-(2H)-benzopyran (1.5 g) and 4-(3,4-dimethoxyphenyl)-piperidine hydrochloride (1.78 g), followed by dry potassium carbonate (1.71 g) and by potassium iodide (1.03 g) in 2-butanone (50 cc). The oil obtained is taken up with ethyl acetate (50 cc). The organic phase is washed with a 1N solution of sodium hydroxide (10 cc) and then with water and is then dried over magnesium sulphate. It is then concentrated to dryness under reduced pressure and the residue is chromatographed on a column 3 cm in diameter, containing silica gel (25 g), using a dichloromethane-acetone mixture (70-30 by volume) as eluent and collecting 100-cc fractions. The first five fractions are concentrated to dryness. The oil obtained is dissolved while hot in the minimum quantity of isopropyl alcohol and then this solution is added to a warm solution of fumaric acid (0.696 g) in isopropyl alcohol. After return to a temperature in the region of 20° C., the crystals formed are filtered off and then recrystallized from isopropanol (100 cc). The A isomer of 1-[2-(3,4-dihydro-1(2H)-benzopyran-4-yl)ethyl]-4-(3,4-dimethoxyphenyl)piperidine fumarate (2.4 g) is thus obtained in the form of a white solid melting at 170° C.

$[\alpha]_D^{20} = -12.3 \pm 0.9°$ (c=0.509, water).

The A isomer of 4-(2-bromoethyl)-3,4-dihydro(2H)-benzopyran may be prepared by following the procedure described in Example 2.

EXAMPLE 17

The B isomer of 1-[2-(3,4-dihydro-1(2H)-benzopyran-4-yl)ethyl]-4-(3,4-dimethoxyphenyl)piperidine fumarate is prepared by following the procedure of Example 16 but starting with the B isomer of 4-(2-bromoethyl)-3,4-dihydro-(2H)-benzopyran (1.5 g) and 4-(3,4-dimethoxyphenyl)piperidine dihydrochloride (1.78 g), followed by potassium carbonate (1.71 g) and potassium iodide (1.03 g) in 2-butanone (50 cc).

The B isomer of 1-[2-(3,4-dihydro-1(2H)-benzopyran-4-yl)-ethyl]-4-(3,4-dimethoxyphenyl)piperidine fumarate (2.4 g) is thus obtained in the form of a white solid melting at 170° C.

$[\alpha]_D^{20} = +11.9 \pm 1.1°$ (c=0.42, water).

EXAMPLE 18

The procedure of Example 1 is followed, starting with 4-(2-bromoethyl)-6-fluoro-3,4-dihydro-(2H)-benzopyran (2 g), with 4-(3,4-dimethoxyphenyl)piperidine hydrochloride (1.99 g) and with dry potassium carbonate (1.06 g), followed by potassium iodide (1.27 g) in 2-butanone (70 cc).

The residue obtained is purified by chromatography on a column 4.4 cm in diameter, containing silica gel (100 g), using a dichloromethane-acetone mixture (50-50 by volume) as eluent and collecting 20-cc fractions. The fractions between 190 and 410 cc are concentrated to dryness. The oil obtained is taken up with ethanol (30 cc) and then a 5.5 N solution of hydrochloric acid in isopropanol (1.46 cc) is added to it. The product obtained (2.44 g) is recrystallized from ethanol (30 cc) and 1-[2-(6-fluoro-3,4-dihydro-1(2H)-benzopyran-4-yl)ethyl]-4-(3,4-dimethoxyphenyl)piperidine hydrochloride (1.7 g) is thus obtained in the form of a white solid melting at 200° C.

4-(2-Bromoethyl)-6-fluoro-3,4-dihydro-(2H)-benzopyran may be prepared by following the procedure of Example 1 but starting with 2-(6-fluoro-3,4-dihydro-1(2H)-benzopyran-4-yl)ethanol (6.32 g), N,N'-carbonyldiimidazole (5.22 g) and from allyl bromide (19.2 cc) in acetonitrile (50 cc). The oil thus obtained is chromatographed on a column 4.4 cm in diameter, containing silica gel (100 g) using dichloromethane (240 cc) as eluent and collecting 30-cc fractions. The fractions between 150 and 240 cc are concentrated to dryness.

4-(2-Bromoethyl)-6-fluoro-3,4-dihydro-(2H)-benzopyran (6.3 g) is thus obtained in the form of a pale yellow oil.

NMR spectrum (250 MHz, CDCL$_3$, δ in ppm): 6.7 to 6.95 (mt, aromatic 3H), 4.17 (mt, —O—CH$_2$—), 3.54 (mt, —CH$_2$—Br), 3.08 (mt, >CH—), 2.33 and 2.06 (mt, —CH$_2$—CH$_2$Br), 2.15 and 1.77 (mt, —CH$_2$— at 3).

2-(6-Fluoro-3,4-dihydro-1(2H)-benzopyran-4-yl)-ethanol may be prepared by following the procedure of Example 1 but starting with lithium aluminium hydride (2.55 g) and ethyl (6-fluoro-3,4-dihydro-1(2H)-benzopyran-4-yl)ethanoate (8 g) in tetrahydrofuran (180 cc). 2-(6-Fluoro-3,4-dihydro-1(2H)-benzopyran-4-yl)ethanol (6.59 g) is thus obtained in the form of a colourless oil.

NMR spectrum (200 MHz, CDCl$_3$, δ in ppm): 6.7 to 6.9 (mt, aromatic 3H), 4.14 (mt, —O—CH$_2$—), 3.85 (mt, —CH$_2$—OH), 3 (mt, >CH—), 1.7–2.2 (mt, —CH$_2$ at -3 and —CH$_2$CH$_2$OH).

Ethyl (6-fluoro-3,4-dihydro-1(2H)-benzopyran-4-yl)ethanoate may be prepared by following the procedure of Example 1 but starting with a mixture of ethyl 6-fluoro-3,4-dihydro-1(2H)-benzopyran-4-ylidene)acetate (14.9 g, E, Z and endo) and with palladium on charcoal (10%, 0.75 g) in methanol (400 cc).

Ethyl (6-fluoro-3,4-dihydro-1(2H)-benzopyran-4-yl)ethanoate (14.6 g) is thus obtained in the form of a pale yellow oil.

NMR spectrum (250 MHz, CDCl$_3$, δ in ppm): 6.75 to 6.90 (mt, aromatic 3H), 4.13 and 4.18 (mt+q, —O—CH$_2$—+—CO—OCH$_2$—CH$_3$), 3.32 (mt, >CH—), 2.51 and 2.75 (mt, >CH—), 7.80 and 2.11 (mt, —CH$_2$— at 3), 1.27 (t, —CO—O—CH$_2$—CH$_3$).

(E,Z and endo) ethyl 6-fluoro-3,4-dihydro-1(2H)-benzopyran-4-ylideneacetate may be prepared by following the procedure of Example 1 but starting with ethyl diethylphosphonoacetate (44.1 g), sodium hydride (80%, 5.37 g) and from 6-fluoro-4-chromanone (11.9 g) [prepared according to the French patent application no. 2,588,860] in tetrahydrofuran (300 cc).

The oil obtained is chromatographed on a 4.4-cm column containing silica gel (100 g), using a cyclohexane-ethyl acetate mixture (90–10 by volume, 0.58 liter) as eluent and collecting 20-cc fractions. The fractions between 100 and 580 cc are concentrated to dryness.

A mixture of E,Z and endo isomers of ethyl 6-fluoro-3,4-dihydro-1(2H)-benzopyran-4-ylideneacetate (15.9 g) is thus obtained in the form of a pale yellow oil.

NMR spectrum (200 MHz, CDCl$_3$, δ in ppm). Characteristic peaks for each of the products:

| | |
|---|---|
| E isomer (65%) | 3.35 (dt, —CH$_2$— at 3) |
| | 6.26 (broad s, —CH=) |
| Z isomer (15%) | 2.61 (dt, —CH$_2$— at 3) |
| | 5.73 (broad s, —CH=) |
| Endo isomer (20%) | 3.35 (s, —CH$_2$—CO$_2$—) |
| | 4.76 (d, —CH$_2$—) |
| | 5.8 (t, —CH=) |

EXAMPLE 19

The procedure is as in Example 1, starting with 4-(2-bromoethyl)-6-chloro-3,4-dihydro-2H-benzopyran (2 g), 4-(3,4-dimethoxyphenyl)piperidine hydrochloride (1.87 g) and dry potassium carbonate (1.07 g), followed by potassium iodide (1.21 g) in 2-butanone (60 cc). The residue obtained is filtered through a column 4.4 cm in diameter, containing silica gel (100 g), using a dichloromethane-acetone mixture (50-50 by volume) as eluent and collecting 30-cc fractions. The fractions between 270 and 540 cc are concentrated to dryness. The oil obtained is taken up with ethanol (30 cc) and a 5.5N solution of hydrochloric acid in isopropanol (1.3 cc) is added, followed by ethyl ether (200 cc).

1-[4-(6-Chloro-3,4-dihydro-1(2H)-benzopyran-4-yl)ethyl]-4-(3,4-dimethoxyphenyl)piperidine hydrochloride (2.74 g) is thus obtained in the form of a solid melting at 191° C.

4-(2-Bromoethyl)-6-chloro-3,4-dihydro-2H-benzopyran may be prepared by proceeding as in Example 1, but starting with 2-(6-chloro-3,4-dihydro-1(2H)-benzopyran-4-yl)ethanol (5.5 g), N,N'-carbonyldiimidazole (4.2 g) and allyl bromide (1.55 cc) in acetonitrile (30 cc). The oil thus obtained is chromatographed on a column 4.4 cm in diameter, containing silica gel (100 g), using a dichloromethane-cyclohexane mixture (30-70) as eluent and collecting 30-cc fractions. The fractions between 180 and 300 cc are concentrated to dryness.

A residue (5.67 g) is obtained and is again repurified by liquid phase chromatography on a column 4 cm in diameter and 30 cm in height containing 40µ silica, using a dichloromethane-cyclohexane mixture (20–80 by volume) as mobile phase and a mobile phase flow rate of 70 cc/min. The fractions between 910 cc and 1,330 cc are concentrated to dryness.

4-(2-Bromoethyl)-6-chloro-3,4-dihydro-2H-benzopyran (3.8 g) is thus obtained in the form of a yellow oil.

NMR spectrum (250 MHz, CDCl$_3$, δ in ppm): 7.13 (d, 1H, aromatic at 5), 7.07 (dd, aromatic at 7), 6.76 (d, 1H, aromatic at 8), 4.19 (mt, 2H, —O—CH$_2$—), 3.55 (mt, 2H, —CH$_2$—Br), 3.08 (mt, 1H, >CH—), 2.34 and 2.06 (mt, —CH$_2$—CH$_2$Br), 2.14 and 1.78 (mt, —CH$_2$— at 3), 2-(6-Chloro-3,4-dihydro-1(2H)-benzopyran-4-yl)ethanol may be prepared by proceeding as in Example 1, but starting with lithium aluminium hydride (1.97 g), and ethyl (6-chloro-3,4-dihydro-1(2H)-benzopyran-4-yl)ethanoate (6.6 g) in tetrahydrofuran (120 cc). 2-(6-methoxy-3,4-dihydro-1(2H)-benzopyran-4-yl)ethanol (5.5 g) is thus obtained in the form of a colourless oil.

NMR spectrum (250 MHz, CDCl$_3$, δ in ppm): 6.75 (d, 1H, aromatic at 8), 7.06 (dd, 1H, aromatic at 7), 7.15 (d, 1H, aromatic at 5), 4.20 (mt, —O—CH$_2$—), 3.82 (t, —CH$_2$—OH), 3.02 (mt, >CH—), 1.85 and 2.13 (mt, —CH$_2$—at —3 and —CH$_2$CH$_2$OH), 1.78 and 2.05 (mt, —CH$_2$CH$_2$OH), 1.55 (s, —O—H), Ethyl (6-chloro-3,4-dihydro-1(2H)-benzopyran-4-yl)ethanoate may be prepared by proceeding as in Example 1 but starting with a mixture (6.83 g) of (E) ethyl 6-chloro-3,4-dihydro-1(2H)-benzopyran-4-ylideneacetate and 10% palladium on charcoal (0.7 g) in ethyl acetate (200 cc).

Ethyl (6-methoxy-3,4-dihydro-1(2H)-benzopyran-4-yl)ethanoate (6.6 g) is thus obtained in the form of a pale yellow oil.

NMR spectrum (400 MHz, CDCl$_3$, δ in ppm): 7.3 (d, 1H, aromatic at 5), 7.23 (dd, 1H, aromatic at 7), 6.92 (d, 1H, aromatic at 8), 4.35 (mt, —CH$_2$—O— and —CO$_2$CH$_2$—), 3.5 (mt, >CH—) 2.7 and 2.95 (dd, —CH$_2$—CO$_2$—), 2.02 and 2.3 (mt, —CH$_2$— at 3), 1.47 (t, —CH$_3$), (E) Ethyl 6-chloro-3,4-dihydro-1(2H)-benzopyran-4-ylideneacetate may be prepared as described in Example 1, but starting with sodium hydride (80%; 4.11 g), ethyl diethylphosohonoacetate (33.7 g) and 6-chloro-4-chromanone (10 g) in tetrahydrofuran (250 cc). The residue obtained is chromatographed on a column 4.4 cm in diameter, containing silica gel (200 g), the mobile phase being a mixture of cyclohexane and ethyl acetate (90-10 by volume). The fractions between 400 cc and 1,120 cc are concentrated to dryness.

Ethyl (6-chloro-3,4-dihydro-1(2H)-benzopyran-4-ylidene)acetate E isomer (containing 3% of Z isomer) (10 g) is thus obtained in the form of a pale yellow oil.

NMR spectrum (250 MHz, CDCl$_3$, δ in ppm): 7.56 (d, 1H, aromatic at 5), 7.2 (dd, 1H, aromatic at 7), 6.82 (d, 1H, aromatic at 8), 6.3 (t, —CH=), 4.22 (mt, —O—CH$_2$— and —CO$_2$—CH$_2$—), 3.37 (td, —CH$_2$— at -3), 1.33 (t, —CH$_3$),

EXAMPLE 20

4-(2-Bromoethyl)-6-hydroxy-3,4-dihydro-2H-benzopyran (2.3 g), 4-(3,4-dimethoxyphenyl)piperidine (5.88 g) and potassium iodide (1.5 g) are heated under reflux in 2-butanone (70 cc) for 1 hour 30 minutes.

The reaction mixture is filtered through sintered glass and the solvent is then evaporated off under reduced pressure (5.2 kPa). The residue obtained is chromatographed on a column 4.4 cm in diameter containing silica gel (100 g), using a dichloromethane-isopropanol mixture (90-10 by volume) as eluent and collecting 20-cc. fractions. The fractions between 200 and 540 cc are concentrated to dryness.

After a first recrystallization from ethanol (30 cc) and a second recrystallization from methanol (30 cc), 1-(3,4-dimethoxyphenyl)-4-[2-(6-hydroxy-3,4-dihydro-1(2H)-benzopyran-4-yl)ethyl]piperidine hydroiodide (1.2 g) is obtained in the form of a white solid melting with decomposition in the region of 200° C.

4-(2-Bromoethyl)-6-hydroxy-3,4-dihydro-2H-benzopyran may be prepared by heating a solution of 4-(2-bromoethyl)-6-methoxy-3,4-dihydro-2H-benzopyran (3 g) in acetic acid (30 cc), to which concentrated hydrobromic acid (30 cc) has been added, for 4 hours.

The reaction mixture is concentrated under reduced pressure (5.2 kPa), concentrated aqueous ammonia is added, and the mixture is extracted with ethyl acetate. The organic phase, dried over anhydrous magnesium sulphate, is then concentrated to dryness. The residue obtained is chromatographed on a column 4.4 cm in diameter containing silica (100 g), using a cyclohexane-ethyl acetate mixture (70-30 by volume) as eluent. The fractions between 220 and 295 cc are concentrated to dryness and 4-(2-bromoethyl)-6-hydroxy-3,4-dihydro-2H-benzopyran is obtained in the form of a pale yellow oil.

NMR spectrum (250 MHz, CDCl$_3$, δ in ppm): 6.65 (mt, 3H, aromatic), 4.7 (s, —O—H), 4.16 (mt, —O—CH$_2$—), 3.53 (mt, —CH$_2$—Br), 3.05 (mt, >CH—), 2.31 and 2.07 (mt, —CH$_2$—CH$_2$—Br), 2.14 and 1.75 (mt, —CH$_2$— at 3).

EXAMPLE 21

The procedure is as in Example 1, starting with 4-(2-bromoethyl)-6-nitro-3,4-dihydro-2H-benzopyran (2 g), 4-(3,4-dimethoxyphenyl)piperidine hydrochloride (1.8 g) and dry potassium carbonate (0.96 g), followed by potassium iodide (1.16 g) in 2-butanone (70 cc).

The residue obtained is purified by chromatography on a column 4.4 cm in diameter, containing silica gel (100 g), using a dichloromethane-ethanol mixture (96-4 by volume) as eluent and collecting 50-cc fractions. The fractions between 0.25 and 1.1 liter are concentrated to dryness. The oil obtained is taken up with ethanol (50 cc), and a 5.5N solution of hydrochloric acid in isopropanol (1.15 cc) is then added to it. The precipitate obtained (1.4 g) is recrystallized from methanol (15 cc). 1-[2-(6-Nitro-3,4-dihydro-1(2H)-benzopyran-4-yl)ethyl]-4-(3,4-dimethoxyphenyl)piperidine hydrochloride (0.9 g) is thus obtained in the form of a white solid melting at 209° C.

4-(2-Bromoethyl)-6-nitro-3,4-dihydro-2H-benzopyran may be prepared as follows:

Concentrated nitric acid (d=1.40; 0.9 cc) is added dropwise to a solution of 4-(2-bromoethyl)-3,4-dihydro-2H-benzopyran (3 g) in acetic acid (8.4 cc), cooled to between 10°-15° C. After 18 hours at 20° C., the reaction mixture is poured onto ice and is then extracted with dichloromethane (200 cc). After several washes with water, the organic phase is dried over magnesium sulphate and is then concentrated to dryness under reduced pressure (5.2 kPa). The residue obtained is chromatographed on a column 4.4 cm in diameter containing silica gel (100 g), using a cyclohexane-ethyl acetate mixture (90-10 by volume) as eluent. The fractions between 630 and 730 cc are concentrated to dryness and 4-(2-bromoethyl)-6-nitro-3,4-dihydro-2H-benzopyran (0.35 g) is thus obtained in the form of a yellow oil.

NMR spectrum (250 MHz, CDCl$_3$, δ in ppm): 8.12 (d, 1H at 5, aromatic), 8.03 (dd, 1H at 7, aromatic), 6.9 (d, 1H at 8, aromatic), 4.32 (mt, 2H, —O—CH$_2$—), 3.55 (mt, 2H, —CH$_2$—Br), 3.20 (mt, 1H, >CH—), 2.4 and 2.10 (mt, —CH$_2$—CH$_2$Br), 2.20 and 1.87 (mt, —CH$_2$—at 3).

EXAMPLE 22

The procedure is as in Example 1, starting with 4-(2-bromoethyl)-2,2-dimethyl-3,4-dihydro-2H-benzopyran (2 g), 4-(3,4-dimethoxyphenyl)piperidine dihydrochloride (1.92 g) and dry potassium carbonate (1 g), followed by potassium iodide (1.23 g) in 2-butanone (70 cc).

The residue obtained is purified by chromatography on a column 4.4 cm in diameter containing silica gel (100 g), using an ethyl acetate-ethanol mixture (90-10 by volume) as eluent and collecting 20-cc fractions. The fractions between 320 and 440 cc are concentrated to dryness. The oil obtained is taken up with ethanol (50 cc) and a 5.5N solution of hydrochloric acid in isopropanol (0.93 cc) is added. The crystals formed are then recrystallized from ethanol (23 cc) and 1-(3,4-dimethoxyphenyl)-4-[2-(2,2-dimethyl-3,4-dihydro-1(2H)-benzopyran-4-yl)ethyl]piperidine hydrochloride (1 g) is thus obtained in the form of white crystals melting at 220° C.

4-(2-Bromoethyl)-2,2-dimethyl-3,4-dihydro-2H-benzopyran may be prepared by proceeding as in Example 1 but starting with 2-(2,2-dimethyl-3,4-dihydro-1(2H)-benzopyran-4-yl)ethanol (7 g), N,N'-carbonyldiimidazole (5.35 g) and allyl bromide (19.8 cc) in acetonitrile (50 cc).

The oil thus obtained is chromatographed on a column 4.4 cm in diameter containing silica gel (100 g), using dichloromethane as eluent and collecting 20-cc fractions. The fractions between 140 and 240 cc are concentrated to dryness.

4-(2-Bromoethyl)-2,2-dimethyl-3,4-dihydro-2H-benzopyran (7.66 g) is obtained in the form of a solid melting at 72° C.

2-(2,2-Dimethyl-3,4-dihydro-1(2H)-benzopyran-4-yl)ethanol may be prepared by proceeding as in Example 1 but starting with lithium aluminium hydride (2.5 g) and ethyl 2-(2,2-dimethyl-3,4-dihydro-1(2H)-benzopyran-4-yl)ethanoate (8.2 g) in tetrahydrofuran (180 cc).

2-(2,2-Dimethyl-3,4-dihydro-1(2H)-benzopyran-4-yl)ethanol (7 g) is thus obtained in the form of a white solid melting in the region of 67° C.

Ethyl 2-(2,2-dimethyl-3,4-dihydro-1(2H)-benzopyran-4-yl)ethanoate may be prepared by proceeding as in Example 1 but starting with ethyl 2,2-dimethyl-3,4-dihydro-1(2H)-benzopyran-4-ylideneacetate (8.4 g) and 10% palladium on charcoal (0.42 g) in ethanol (200 cc).

Ethyl 2-(2,2-dimethyl-3,4-dihydro-1(2H)-benzopyran-4-yl)ethanoate (8.2 g) is thus obtained in the form of a pale yellow oil.

NMR spectrum (200 MHz, CDCl$_3$, δ in ppm): 7.12 and 6.85 (mt, 4H, aromatics), 4.2 (q, —CO$_2$—CH$_2$—), 3.37 (mt, >CH—), 3 and 2.38 (dd, —CH$_2$—CO$_2$—), 2 and 1.60 (dd and t, —CH$_2$— at 3), 1.43 and 1.27 (s, >C(CH$_3$)$_2$), 1.28 (t, —CH$_2$—CH$_3$).

Ethyl 2,2-dimethyl-3,4-dihydro-1(2H)-benzopyran-4-ylideneacetate may be prepared by proceeding as in Example 1, but starting with sodium hydride (80%; 4.7 g), ethyl diethylphosphoacetate (3.8 g) and 2,2-dimethyl-4-chromanone (10 g) in dimethoxyethane (200 cc).

The residue obtained is chromatographed on a column 4.4 cm in diameter containing silica gel (100 g), using a cyclohexane-ethyl acetate mixture (95-5 by volume) as eluent and collecting the fractions between 150 and 510 cc.

A mixture of ethyl 2,2-dimethyl-3,4-dihydro-1(2H)-benzopyran-4-ylideneacetate isomers (9.5 g) is thus obtained in the form of a pale yellow oil.

| NMR spectrum (250 MHx, CDCl$_3$, δ in ppm) | |
|---|---|
| E isomer (40%) | 7.59 (dd, 1H, aromatic) <br> 6.41 (t, —CH=) <br> 3.3 (d, —CH$_2$— at 3) |
| Z isomer (40%) | 7.87 (dd, 1H, aromatic) <br> 5.7 (s, —CH=) <br> 2.47 (s, —CH$_2$— at 3) |
| Endo isomer (20%) | 5.58 (s, —CH=) <br> 3.4 (s, —CH$_2$—CO$_2$—) |

2,2-Dimethyl-4-chromanone may be prepared according to the method described in Belgian Patent 844,943.

EXAMPLE 23

The procedure is as in Example 1, starting with 4-(2-bromoethyl)-3,4-dihydro-2H-benxopyran (2 g), 1-(3,4-methylenedioxyphenyl)piperazine dihydrochloride (2.3 g) and dry potassium carbonate (2.28 g), followed by potassium iodide (1.4 g) in 2-butanone (70 cc).

After chromatography of the residue on a column 4.4 cm in diameter, containing silica gel (100 g), using ethyl acetate as eluent and collecting 30-cc fractions, an oil is isolated by concentrating the fractions between 210 and 360 cc, and is crystallized from ethanol (40 cc) to which a 5N solution of hydrochloric acid in isopropanol (2.4 cc) has been added.

White crystals of 1-[2-(3,4-dihydro-1(2H)-benzopyran-4-yl)ethyl]-4-(3,4-methylenedioxyphenyl)piperazine dihydrochloride (2.18 g) are thus obtained; their melting point is in the neighbourhood of 180° C.

EXAMPLE 24

The procedure is as in Example 1, starting with 4-(2-bromoethyl)-3,4-dihydro-2H-benxopyran (2 g), 6-(1-piperazinyl)-1,4-benzodioxane dihydrochloride (2.43 g) and dry potassium carbonate (2.28 g), followed by potassium iodide (3.4 g) in 2-butanone (70 cc).

The residue obtained is purified by chromatography on a column 4.4 cm in diameter containing silica gel (100 g), using ethyl acetate (800 cc) as eluent and collecting 20-cc fractions. The fractions between 300 and 680 cc are concentrated to dryness. The oil obtained (1.6 g) is taken up with ethanol (20 cc) and a 5N solution of hydrochloric acid in isopropanol (1.7 cc) is then added to it. The crystals obtained are taken up in methanol (30 cc) and the solution is heated to reflux, filtered hot and precipitation is carried out by adding ethyl ether (50 cc).

6-{4-[2-(3,4-Dihydro-1(2H)-benzopyran-4-yl)ethyl]1-piperazinyl}-1,4-benzodioxane dihydrochloride (0.9 g) is thus obtained.

6-(1-Piperazinyl)-1,4-benzodioxane dihydrochloride may be prepared as follows:

6-Amino-1,4-benzodioxane (30.2 g) and bis(2-chloroethyl)amine hydrochloride (42.84 g) are dissolved in 2-butanol (300 cc) and refluxed for 2 hours. Dry potassium carbonate (27.6 g) is added to the solution, cooled to 80° C., and the resulting mixture is refluxed for 18 hours. After cooling, the precipitate formed is filtered off and is washed with acetone and the insoluble material is dissolved in water (500 cc) and is neutralized with concentrated sodium hydroxide and then extracted with dichloromethane (400 cc). The organic phase is then dried over magnesium sulphate and, after filtration, concentrated under reduced pressure (5.2 kPa).

The oil obtained is taken up with ethanol (50 cc) and a 5N solution of hydrochloric acid in isopropanol (100 cc) is added. The precipitate formed is then heated to boiling in methanol (1 liter). After cooling, the crystals formed are filtered off and 6-(1-piperazinyl)-1,4-benzodioxane dihydrochloride (36.9 g) is thus obtained in the form of a solid melting with decomposition at 205° C.

EXAMPLE 25

The procedure is as in Example 1, starting with 4-(2-bromoethyl)-3,4-dihydro-2H-benxopyran (10 g), 1-(3-methoxy-4-nitrophenyl)piperazine (9.87 g) and dry potassium carbonate (5.75 g), followed by potassium iodide (6.9 g) in 2-butanone (150 cc) and refluxing for 8 hours.

The residue obtained is purified by chromatography on a column 5 cm in diameter, containing silica gel (400 g), the eluent employed being first pure dichloromethane (1 liter) and then a dichloromethane-methanol mixture (97-3 by volume), and collecting 125-cc fractions. The fractions between 2 liters and 3.125 liters are concentrated to dryness to give an orange-coloured oil (16.1 g). This oil is taken up with acetone (250 cc) and the hydrochloride is formed by adding a 5N solution of hydrochloric acid in isopropanol (16 cc). After 1 hour at rest at 10° C., filtering and washing with acetone (2×50 cc) followed by ethyl ether (50 cc), a yellow solid (11.9 g) is obtained. This solid is recrystallized from boiling methanol (100 cc). After standing for 30 minutes at 20° C., the crystals are filtered off and are washed with methanol (2×10 cc) and then with ethyl ether (25 cc).

1-[2-(3,4-Dihydro-1(2H)-benzopyran-4-yl)ethyl]4-(3-methoxy-4-nitrophenyl)piperazine hydrochloride (9.45 g) is obtained in the form of a yellow solid melting at 175° C.

1-(3-Methoxy-4-nitrophenyl)piperazine may be prepared as follows:

A mixture of 5-chloro-2-nitroanisole (25 g), anhydrous piperazine (55 g) and toluene (20 cc) is refluxed gently for 45 minutes.

The hot reaction mixture is poured into distilled water (500 cc) and toluene (100 cc). After 30 minutes' stirring, the lukewarm reaction mixture is filtered and washed with water (2×50 cc) and then with ethyl ether (2×50 cc).

1-(3-Methoxy-4-nitrophenyl)piperazine (9.87 g) is obtained in the form of a yellow solid melting at 135° C.

EXAMPLE 26

The procedure is as in Example 1, but starting with 4-(2-bromoethyl)-3,4-dihydro-2H-benzopyran (1.5 g), 4-benzylpiperidine (1.02 g) and dry potassium carbonate (0.8 g), followed by potassium iodide (1 g) in 2-butanone (50 cc).

The oil obtained is taken up with ethanol (30 cc) and a 2N solution of hydrochloric acid in ethanol (1.6 cc) is added.

1-[2-(3,4-Dihydro-1(2H)-benzopyran-4-yl)ethyl]-4-benzylpiperidine hydrochloride (1.15 g) is thus obtained in the form of a white solid melting at 210° C.

EXAMPLE 27

The procedure is as in Example 1, starting with 4-(2-bromoethyl)-3,4-dihydro-2H-benzopyran (1.7 g), 1-(4-methylphenylmethyl)piperazine (1.8 g) and dry potassium carbonate (1.93 g), followed by potassium iodide (1.15 g) in 2-butanone (50 cc).

The residue obtained is purified by chromatography on a column 4.4 cm in diameter, containing silica gel (75 g), using ethyl acetate as eluent. The fractions between 700 and 1,000 cc are concentrated to dryness. The oil obtained is taken up with ethanol (20 cc) and a 2N solution of hydrochloric acid (5.5 cc) is then added to it. 1-[2-(3,4-Dihydro-1(2H)-benzopyran-4-yl)-ethyl]-4-(4-methylphenylmethyl)piperazine dihydrochloride (2.05 g) is obtained in the form of a white solid whose melting point is 230° C.

1-(4-Methylphenylmethyl)piperazine may be prepared according to the method described in U.S. Pat. No. 4,421,753.

EXAMPLE 28

The procedure is as in Example 1, starting with 4-(2-bromoethyl)-3,4-dihydro-2H-benzopyran (2 g), 1-(3,4-dimethoxyphenylmethyl)piperazine dihydrochloride (2.56 g) and dry potassium carbonate (2.52 g), followed by potassium iodide (3 g) in 2-butanone (70 cc). The oil obtained is purified by chromatography on a column 4.4 cm in diameter containing silica gel (100 g), using ethyl acetate (900 cc) as eluent and collecting 50-cc fractions. The fractions between 700 and 900 cc are concentrated to dryness. The oil obtained is taken up with ethanol (30 cc) and a 5N solution of hydrochloric acid in isopropanol (3.3 cc) is then added to it. The precipitate filtered off leads to 1-[2-(3,4-dihydro-1(2H)-benzopyran-4-yl)ethyl]-4-(3,4-dimethoxyphenylmethyl)piperazine dihydrochloride (2.5 g) in the form of a white solid melting at 250° C.

1-(3,4-Dimethoxyphenylmethyl)piperazine dihydrochloride may be prepared according to Japanese patent application no. 82/093,962.

EXAMPLE 29

The procedure is as in Example 1, starting with 4-(2-bromoethyl)-3,4-dihydro-2H-benzopyran (1.31 g), 4-(3,4-dimethoxyphenylmethyl)piperidine (1.28 g) and dry potassium carbonate (0.35 g), followed by potassium iodide (0.9 g) in 2-butanone (70 cc).

The residue obtained is purified by chromatography on a column 5.5 cm in diameter, containing silica gel (50 g), using ethyl acetate (510 cc) as eluent and collecting 30-cc fractions. The fractions between 180 and 510 cc are concentrated to dryness. The oil obtained is taken up with ethanol (20 cc) and a 5N solution of hydrochloric acid in isopropanol (0.7 cc) is then added to it.

On adding ethyl ether (200 cc), 1-[2-(3,4-dihydro-1(2H)-benzopyran)-4-yl)ethyl]-4-(3,4-dimethoxyphenylmethyl)piperidine hydrochloride (1.26 g) is obtained in the form of a white solid melting at 184° C.

4-(3,4-Dimethoxyphenylmethyl)piperidine is prepared by hydrogenation at 20° C., under two atmospheres, in the presence of palladium hydroxide (0.042 g), of 4-(3,4-dimethoxybenzylidene)-1-phenylmethylpiperidine (0.42 g) in methanol (100 cc), to which a 5N solution of hydrochloric acid in isopropanol (0.26 cc) has been added. After filtration and evaporation of the solvent under reduced pressure, 4-(3,4-dimethoxyphenylmethyl)-piperidine (0.3 g) is isolated in the form of a white solid whose melting point is 76° C.

4-(3,4-Dimethoxybenzylidene)-1-phenylmethylpiperidine may be prepared as follows:

The phosphorus ylide obtained by stirring 3,4-dimethoxyphenylmethyltriphenylphosphonium bromide (16.8 g) and potassium tert-butylate (3.82 g) in toluene (50 cc) at ambient temperature (4 hours) is added to 1-phenylmethyl-4-piperidinone (4.9 g) in toluene (100 cc) heated to 90° C.

After 3 hours' heating, the material is taken up with 6N hydrochloric acid (50 cc). After neutralization, the aqueous phase is extracted with dichloromethane (2×400 cc). The organic phase is then dried over magnesium sulphate and then concentrated to dryness under reduced pressure.

The residue obtained is chromatographed on a column 5.5 cm in diameter containing silica gel (150 g), using a cyclohexane-ethyl acetate mixture (50-50 by volume) as eluent and collecting 30-cc fractions. The fractions between 360 and 750 cc are concentrated to dryness.

4-(3,4-Dimethoxybenzylidene)-1-phenylmethylpiperidine (5.6 g) is then obtained in the form of a white solid melting at 91° C.

3,4-Dimethoxyphenylmethyltriphenylphosphonium bromide may be prepared as follows:

3,4-Dimethoxy-α-bromotoluene (11.6 g) [Gordon N. Walker et al., J. Org. Chem., 26, 2740 (1961)] and triphenylphosphine (13.11 g) are heated in dimethylformamide (150 cc) at 75° C. for 1 hour 30 minutes. After addition of ethyl ether (700 cc) to the reaction mixture and filtration, 3,4-dimethoxyphenylmethyltriphenylphosphonium bromide (19.8 g) is obtained in the form of a white solid melting at 260° C.

EXAMPLE 30

The procedure is as in Example 1, but starting with 4-(2-bromoethyl)-3,4-dihydro-2H-benzopyran (2g), 4-pyridylpiperazine (2.76 g) and potassium iodide (1.37 g) in 2-butanone (70 cc).

The crude product obtained is purified by chromatography on a column 4.4 cm in diameter, containing silica gel (50 g), using a toluene-diethylamine mixture (95-5 by volume) as eluent. The first 600 cc are concentrated to dryness. The oil obtained is taken up with ethanol (20 cc) and a 5.5N solution of hydrochloric acid in isopropanol (1.6 cc) is then added to it. Crystals (0.7 g) are obtained and are recrystallized twice from aqueous ethanol (97.5-2.5 by volume) and 1-[2-(3,4-dihydro-1(2H)-benzopyran-4-yl)ethyl]-4-pyridylpiperazine dihydrochloride (0.41 g) is thus isolated in the form of a white solid melting at 250° C.

EXAMPLE 31

The procedure is as in Example 1, starting with 4-(2-bromoethyl)-3,4-dihydro-2H-benzopyran (2 g), 1-(4-piperidinyl)-1,3-dihydro-2(2H)-benzimidazolone (1.953 g) and dry potassium carbonate (1.15 g), followed by potassium iodide (1.38 g) in 2-butanone (65 cc).

The residue obtained is extracted with ethyl ether (300 cc), is washed with an aqueous solution (1N) of sodium hydroxide (10 cc) and then with water (20 cc) and is dried over magnesium sulphate.

A hot solution of fumaric acid (0.9 g) dissolved in the minimum quantity of isopropanol is added to the residue obtained, dissolved in the minimum quantity of isopropanol. The mixture is left overnight at 20° C., the crystals obtained are filtered off and are then recrystallized from an aqueous methanol mixture (50–50 by volume).

1-{1-[2-(3,4-dihydro-1(2H)-benzopyran-4-yl)ethyl]4-piperidinyl}-1,3-dihydro-2(2H)-benzimidazolone hydrogen fumarate (2.55 g) is thus obtained in the form of a white solid melting at 260° C.

EXAMPLE 32

1-[2-(3,4-Dihydro-1(2H)-benzopyran-4-yl)ethyl]-4-(4-methoxyphenyl)piperazine dihydrochloride (10 g) is refluxed for 7 hours 45 minutes in a solution of concentrated hydrobromic acid (150 cc) and pure acetic acid (150 cc). The reaction mixture is concentrated under reduced pressure (5.2 kPa), concentrated aqueous ammonia is added, and then the mixture is extracted with ethyl acetate. The organic phase, dried over anhydrous magnesium sulphate, is then concentrated to dryness.

The residue obtained is chromatographed on a column 3.5 cm in diameter, containing silica gel (250 g), using a dichloromethane-ethanol mixture (96-4 by volume) (1.2 liters) and a dichloromethane-ethanol mixture (90-10 by volume, 1 liter) as eluent. The fractions between 1.2 liters and 1.6 liters are concentrated to dryness.

The residue obtained is taken up in the minimum quantity of ethanol and a 5N solution of hydrochloric acid in isopropanol (8 cc) is added. The precipitate obtained by adding ethyl ether is then recrystallized from aqueous ethanol (98-2 by volume; 130 cc). 1-[2-(3,4-Dihydro-1(2H)-benzopyran-4-yl)ethyl]-4-(4-hydroxyphenyl)-piperazine dihydrochloride (3 g) is thus obtained in the form of a white solid melting at 200° C. with decomposition.

EXAMPLE 33

1-[4-(3,4-Dihydro-1(2H)-benzopyranyl)ethyl]-4-(3-methoxyphenyl)piperazine (1.9 g) is heated to 100° C. for 2 hours in concentrated hydrobromic acid (50 cc). After cooling the reaction mixture and adding acetone (100 cc), followed by filtration, 1-[4-(3,4-dihydro-1(2H)benzopyranyl)ethyl]-4-(3-hydroxyphenyl)piperidine hydrobromide (1.8 g) is isolated in the form of a slightly pink solid melting at 240° C.

EXAMPLE 34

1-[2-(3,4-Dihydro-1(2H)-benzopyran-4-yl)ethyl]4-(4-nitrophenyl)piperazine (13.5 g) in ethanol (360 cc), to which concentrated hydrochloric acid (15 cc) has been added, is hydrogenated at 20° C. at atmospheric pressure, in the presence of 10% palladium on charcoal (1.5 g).

After filtration, concentration under reduced pressure (5.2 kPa) is performed until crystallization begins. The crystals thus formed are recrystallized from ethanol (200 cc).

1-(4-Aminophenyl)-4-[2-(3,4-dihydro-1(2H)-benzopyran-4-yl)ethyl]piperazine dihydrochloride (9.6 g) is thus obtained in the form of a greyish solid melting at 210° C. with decomposition.

EXAMPLE 35

1-[2-(3,4-Dihydro-1(2H)-benzopyran-4-yl)ethyl]1-(4-nitrophenyl)piperazine (7.22 g) in acetic acid (300 cc) is hydrogenated at 20° C. at a pressure of 2.7 atmospheres in the presence of 10% palladium on charcoal (0.72 g).

After filtration, the mixture is concentrated under reduced pressure (5.2 kPa) and dichloromethane (150 cc) is added, followed by a 1N aqueous solution of sodium hydroxide (60 cc). After extraction, the organic phase is washed with water (100 cc), and is then dried over magnesium sulphate and concentrated to dryness. The oil obtained is chromatographed on a column 4.4 cm in diameter containing silica gel (100 g), using an ethyl acetate-ethanol mixture (90-10 by volume) as eluent. The fractions between 240 and 600 cc are concentrated to dryness. The oil isolated is crystallized from ethanol (30 cc), after the addition of a 5.5N solution of hydrochloric acid in isopropanol (3.1 cc). After two recrystallizations from aqueous ethanol (37-63 by volume; 20 cc), 4-(4-aminophenyl)-1-[2-(3,4-dihydro-1(2H)-benzopyran-4-yl)ethyl]piperidine hydrochloride (2.13 g) is obtained in the form of a white solid melting at 210° C. with decomposition.

EXAMPLE 36

The procedure is as in Example 16, starting with 1-[2-(3,4-dihydro-1(2H)-benzopyran-4-yl)ethyl]-4-(3-methoxy-4-nitrophenyl)piperazine hydrochloride (6.51 g) in ethanol (160 cc), to which a solution of concentrated hydrochloric acid (6 cc) has been added. The hydrogenation is carried out at 40° C. at atmospheric pressure in the presence of 10% palladium on charcoal (0.5 g).

Distilled water (20 cc) is added to the reaction mixture, which is then filtered. Concentration is performed under reduced pressure (5.2 kPa) until crystallization begins.

A solid (6.5 g) is thus obtained and is recrystallized from aqueous ethanol (5-1 by volume; 60 cc). 1-(4-Amino-3-methoxyphenyl)-4-[2-(3,4-dihydro-1(2H)-benzopyran-4-yl)ethyl]piperazine dihydrate dihydrochloride (6.3 g) is thus obtained in the form of a slightly greyish solid melting with decomposition at 200° C.

EXAMPLE 37

1-[2-(3,4-Dihydro-1(2H)-benzopyran-4-yl)ethyl]-4-(4-nitrobenzoyl)piperazine hydrochloride (5 g) in ethanol (350 cc) is hydrogenated at 20° C. at atmospheric pressure in the presence of 10% palladium on charcoal (0.5 g) and of a 5N solution of hydrochloric acid in isopropanol (10 cc).

After filtration, the mixture is concentrated under reduced pressure (5.2 kPa) down to 50 cc. The crystals formed are recrystallized from ethanol (40 cc).

1-(4-Aminobenzoyl)-4-[2-(3,4-dihydro-1(2H)-benzopyran-4-yl)ethyl]piperazine hydrochloride (1.9 g) is thus obtained in the form of a white solid melting at 205° C.

EXAMPLE 38

1-[2-(6-Nitro-3,4-dihydro-1(2H)-benzopyran-4-yl)ethyl]-4-(3,4-dimethoxyphenyl)piperidine (5.48 g) in ethanol (50 cc), to which a 5.5N solution of hydrochloric acid in isopropanol (11.6 cc) has been added, is hydrogenated at 50° C. at atmospheric pressure in the presence of 10% palladium on charcoal (0.54 g).

After filtration, the mixture is concentrated under reduced pressure (5.2 kPa) and the residue is extracted with dichloromethane (150 cc), is neutralized with a 1N solution of sodium hydroxide (15 cc) and is then washed with water. The organic phase is then dried over magnesium sulphate and then concentrated under reduced pressure (5.2 kPa). The residue obtained is chromatographed on a column 4.4 cm in diameter containing silica gel (100 g), using a dichloromethane-isopropanol mixture (90-10 by volume) as eluent and collecting the fractions between 0.36 and 1.475 liters.

The oil obtained is dissolved in hot ethanol (125 cc), and this solution is then added to a solution of fumaric acid (0.85 g) in ethanol (15 cc). The solution is concentrated under reduced pressure until crystallization begins and the crystals formed are then taken up in a hot solution of ethanol (125 cc). After filtration and cooling, ethyl ether (50 cc) is added to the filtrate, the black precipitate formed is removed, and then more ethyl ether (100 cc) is added.

1-[(6-Amino-3,4-dihydro-1(2H)-benzopyran-4-yl)ethyl]-4-(3,4-dimethoxyphenyl)piperidine fumarate (0.38 g) is thus obtained in the form of a cream solid melting at 198° C.

EXAMPLE 39

Triethylamine (4.9 cc) is added to a solution of 4-(4-aminophenyl)-1-[2-(3,4-dihydro-1(2H)-benzopyran-4-yl)ethyl]piperazine dihydrochloride (4.7 g) in dichloromethane (110 cc), cooled to between 0° and 5° C., and then methanesulphonyl chloride (1 cc) is introduced. After 1 hour the reaction mixture is taken up with water (80 cc) and is extracted with dichloromethane (3×40 cc). The organic phase, washed with sodium hydroxide (N, 10 cc) and then with water, is dried over magnesium sulphate. After filtration, the solution is concentrated to dryness under reduced pressure (5.2 kPa). The residue obtained is chromatographed on a column 4.4 cm in diameter containing silica gel (100 g), using a dichloromethane-ethanol mixture (95-5 by volume) as eluent and collecting 20-cc fractions. The fractions between 500 and 700 cc are concentrated to dryness. The residue obtained is taken up with methanol (100 cc) and a 5.5N solution of hydrochloric acid in isopropanol (2.4 cc) is added to it, and it is then heated to boiling.

After cooling, 1-[2-(3,4-dihydro-1(2H)-benzopyran-4-yl)ethyl]-4-(4-methylsulphonamidophenyl)piperazine hydrochloride (1.3 g) is obtained in the form of a white solid melting at 246° C.

EXAMPLE 40

The procedure is as in Example 39, but starting with 4-(4-aminophenyl)-1-[2-(3,4-dihydro-1(2H)-benzopyran-4-yl)ethyl]piperidine (0.37 g) in dichloromethane (10 cc), triethylamine (0.155 cc), and then methanesulphonyl chloride (0.087 cc).

The residue obtained is chromatographed on a column 3 cm in diameter, containing silica gel (50 g), using a toluene, diethylamine and ethanol mixture (90-5-5 by volume) as eluent and collecting the fractions between 180 and 300 cc. The oil obtained is taken up with ethyl ether. The organic phase is washed with water and dried over magnesium sulphate. After concentration to dryness under reduced pressure (5.2 kPa), the oil isolated crystallizes from ethanol (8 cc) to which a 5.5N solution of hydrochloric acid in isopropanol (0.4 cc) has been added.

After a recrystallization from methanol (5 cc), 1-[2-(3,4-dihydro-1(2H)-benzopyran-4-yl)ethyl]-4-(4-methylsulphonamidophenyl)piperidine hydrochloride (0.17 g) is obtained in the form of a white solid melting at 240° C.

EXAMPLE 41

The procedure is as in Example 39, starting with 1-(4-amino-3-methoxyphenyl)-4-[2-(3,4-dihydro-1(2H)-benzopyran)-4-yl)ethyl]piperazine dihydrate dihydrochloride (3.8 g), triethylamine (7 cc) and methanesulphonyl chloride (2.6 cc) in trichloromethane (60 cc), at −10° C.

After 1 hour, the reaction mixture is concentrated under reduced pressure (5.2 kPa). The residue is taken up with ethanol (60 cc) and a 1N solution of hydrochloric acid (20 cc), and is then concentrated until crystallization begins.

Crystals (3 g) are obtained and are recrystallized twice from aqueous ethanol (98–2 by volume, 50 cc). After filtration, 1-[2-(3,4-dihydro-1(2H)-benzopyran-4-yl)ethyl]-4-(4-methylsulphonamido-3-methoxyphenyl)piperazine dihydrochloride (2.4 g) is obtained in the form of a white solid melting at 180° C.

EXAMPLE 42

The procedure is as in Example 39, but starting with 4-(4-aminophenyl)-1-[2-(3,4-dihydro-1(2H)-benzopyran-4-yl)ethyl]piperidine (3 g) in dichloromethane (66 cc), triethylamine (1.6 cc) and then methanesulphonyl chloride (1.8 cc), for 18 hours at 20° C.

The oil obtained is taken up with ethanol (70 cc) and then a 5.5N solution of hydrochloric acid in isopropanol (1.5 cc) is added to it. The crystals formed are then recrystallized from an ethanol-water solution (50-6 by volume, 56 cc) and 4-[4-bis(methylsulphonyl)aminophenyl]-1-[2-(3,4-dihydro-1(2H)-benzopyran-4-yl)ethyl]piperidine hydrochloride (1.4 g) is thus obtained in the form of a white solid melting at 240° C.

EXAMPLE 43

Acetyl chloride (3 cc) in trichloromethane (3 cc) is added to a solution of 1-(4-aminophenyl)-4-[2-(3,4-dihydro-1(2H)-benzopyran-4-yl)ethyl]piperazine dihydrochloride (2 g) in trichloromethane (15 cc), cooled to 5° C.

After 2 hours, the reaction mixture is concentrated under reduced pressure (5.2 kPa) and is taken up in distilled water (10 cc). The water is separated off and the residual oil is recrystallized from aqueous ethanol (5–10 by volume, 15 cc). After slow crystallization at 20° C., the crystals are washed with aqueous ethanol (5-5 by volume, 3×5 cc), and then with ethyl ether (10 cc). After three recrystallizations from absolute ethanol, 1-(4-acetamidophenyl)-4-[2-(3,4-dihydro-1(2H)benzo-pyran-4-yl)ethyl]piperazine (1.25 g) is obtained in the form of a slightly grey solid melting at 160° C.

EXAMPLE 44

The procedure is as in Example 39, but starting with 1-(4-aminobenzoyl)-4-[2-(3,4-dihydro-1(2H)-benzopy-ran-4-yl)ethyl]piperazine (2.6 g), triethylamine (1 cc) and methanesulphonyl chloride (0.61 cc) in dichloromethane (86 cc).

The residue obtained is chromatographed on a column 4.4 cm in diameter containing silica gel (100 g), using a mixture of trichloromethane, isopropanol and diethylamine (90-5-5 by volume) as eluent and collecting 50-cc fractions. The fractions between 0.55 liter and 1.3 liters are concentrated to dryness.

The product obtained is taken up in dichloromethane, is washed with water, and then the organic phase is dried over magnesium sulphate. After evaporation of the solvent, a solid is obtained, which is dissolved in boiling ethanol (50 cc). A 5.5N solution of hydrochloric acid in isopropanol (0.75 cc) is added. After cooling and recrystallization, 1-[2-(3,4-dihydro-1(2H)-benzopyran-4-yl)ethyl]-4-(4-methanesulphonamidobenzoyl)piperi-dine hydrochloride (1.37 g) is obtained in the form of a white solid melting in the region of 260° C.

EXAMPLE 45

The procedure is as in Example 39, but starting with 1-[(6-amino-3,4-dihydro-1(2H)-benzopyran-4-yl)e-thyl]4-(3,4-dimethoxyphenyl)piperidine (1.2 g) in dichloromethane (45 cc), triethylamine (0.43 cc) and methanesulphonyl chloride (0.24 cc).

The residue obtained is chromatographed on a column 4.4 cm in diameter, containing silica gel (100 g), using a dichloromethane-isopropanol mixture (90-10 by volume) as eluent and collecting 20-cc fractions. The fractions between 500 and 700 cc are concentrated to dryness.

The residue obtained is dissolved in dichloromethane and a mixture of ethanol and methanol (50-50 by volume, 100 cc) is added to it, and it is concentrated under reduced pressure (5.2 kPa) until crystallization begins.

1-[(6-Methylsulphonamido-3,4-dihydro-1(2H)-benzo-pyran-4-yl)ethyl]-4-(3,4-dimethoxyphenyl)piperidine (0.7 g) is thus obtained in the form of a white solid melting at 195° C.

EXAMPLE 46

Triethylamine (3.77 cc) is added to a solution of 1-[2-(3,4-dihydro-1(2H)-benzopyran-4-yl)ethyl]piperazine (6 g) in dichloromethane (100 cc) cooled to between 0° and 5° C., and then para-nitrobenzoyl chloride (4.5 g) is introduced in dichloromethane (10 cc).

After 2 hours at 20° C., the mixture is diluted with distilled water, the organic phase is separated off and is washed with a 1N sodium hydroxide solution (20 cc) and then with water. The organic phase is dried over magnesium sulphate and is then concentrated to dryness. The residue obtained is chromatographed on a column 4.4 cm in diameter containing silica gel (100 g), using a dichloromethane-ethanol mixture (95-5 by volume) as eluent. The fractions between 150 and 520 cc are concentrated to dryness. The residue obtained is taken up in a mixture of ethanol and methanol (50-30 by volume, 100 cc) and a 5.5N solution of hydrochloric acid in isopropanol (3.9 cc) is added. After recrystallization of the crystals obtained in an aqueous ethanol solution (8-92 by volume, 100 cc), 1-[2-(3,4-dihydro-1(2H)-benzopyran-4-yl)ethyl]-4-(4-nitrobenzoyl)piperazine hydrochloride (6.8 g) is obtained in the form of a white solid melting at 146° C.

1-[2-(3,4-Dihydro-1(2H)-benzopyran-4-yl)ethyl]pip-erazine may be prepared as follows:

The procedure is as in Example 1, starting with 4-(2-bromoethyl)-3,4-dihydro-2H-benzopyran (9.7 g), piperazine (10.4 g) and then potassium iodide (13.4 g) in 2-butanone (300 cc), but without the addition of potassium carbonate. The oil obtained is chromatographed on a column 4.4 cm in diameter, containing silica gel (100 g), a mixture of dichloromethane, ethanol and diethylamine (80-18-2 by volume) being used as eluent. The fractions between 200 and 500 cc are concentrated to dryness.

1-[2-(3,4-Dihydro-1(2H)-benzopyran-4-yl)ethyl]-pip-erazine (7.1 g) is thus obtained in the form of an oil which is employed as such in the following stage.

EXAMPLE 47

The procedure is as in Example 46, starting with 1-[2-(3,4-dihydro-1(2H)-benzopyran-4-yl)ethyl]pipera-zine (3.27 g), triethylamine (2.2 cc) and 3,4-dimethoxybenzoyl chloride (2.66 g) in dichloromethane (50 cc).

The residue obtained is chromatographed on a column 4.4 cm in diameter, containing silica gel (100 g), using ethyl acetate as eluent and collecting the fractions between 610 and 900 cc. The residue obtained is taken up in ethanol (110 cc) and a solution (5N) of hydrochloric acid in isopropanol (1.5 cc) is added and the solution is concentrated under reduced pressure (5.2 kPa). The crystals obtained are taken up in a mixture of isopropanol and 2-butanone (50-50 by volume, 30 cc), an insoluble material is filtered off hot, ethyl ether (40 cc) is then added the filtrate, and 1-[2-(3,4-dihydro-1(2H)-benzo-pyran-4yl)ethyl]-4-(3,4-dimethoxybenzoyl)piperazine hydrochilc ride (0.97 g) is thus obtained in the form of a white solid melting at 175° C.

EXAMPLE 48

4-(2-Bromoethyl)-3,4-dihydro-2H-benzopyran (0.23 g), 4-(3-hydroxy-4-methoxyphenyl)piperidine (0.34 g) and potassium iodide (0.136 g) are refluxed for 15 hours in 2-butanone (35 cc). The reaction mixture is filtered through sintered glass and the solvent is then evaporated off under reduced pressure (5.2 kPa) and the oil obtained is taken up with a 20% strength solution (30 cc) of aqueous ammonia. After extraction with ethyl acetate (40 cc), the organic phase is then dried over magnesium sulphate. After evaporation, a brown viscous oil is obtained, which is chromatographed on a column 2 cm in diameter, containing silica gel (15 g), using a dichloromethaneisopropanol mixture (90-10 by volume; 125 cc) as eluent and collecting 25-cc fractions. The fractions between 25 cc and 125 cc are concentrated to dryness. A lukewarm solution of oxalic acid (73 mg) dissolved in ethanol (2 cc) is added to the residue obtained, dissolved in ethanol (3 cc), and the solution is then concentrated under reduced pressure down to approximately 1 cc and 2-butanone (2 cc) and 4 volumes of isopropyl ether are added. After scratching, while keeping lukewarm, a paste is obtained, followed by crystals which are taken up with a hot mixture of 2-butanone and isopropyl ether (50-50 by volume; 8 cc).

After cooling, the crystals formed are filtered off and 1-[2-(3,4-dihydro-1(2H)-benzopyran-4-yl)ethyl]-4-(3-hydroxy-4-methoxyphenyl)piperidine hydrogen oxalate (0.25 g) is obtained in the form of a cream solid melting in the neighbourhood of 152° C.

4-(3-Hydroxy-4-methoxyphenyl)piperidine may be prepared in the following manner:

N-Benzyl-4-(3-hydroxy-4-methoxyphenyl)-1,2,3,6-tetrahydropyridine (0.73 g) in an ethanol-methanol mixture (83-17 by volume; 18 cc) is hydrogenated at 17° C. for 20 hours, under 5 atmospheres, in the presence of palladium hydroxide (0.4 g).

After filtration on a sinter and concentration to dryness under reduced pressure (5.2 kPa), a grey solid (0.4 g) is obtained, which is then chromatographed on a column 2.5 cm in diameter, containing silica (32–63 μ; 67 g), using a toluene-ethanoldiethylamine mixture (60-20-20 by volume; 690 cc) as eluent and collecting 20-cc fractions. The fractions between 450 cc and 690 cc, concentrated to dryness, yield 4-(3-hydroxy-4-methoxyphenyl)piperidine (0.34 g) in the form of a cream solid melting at 250° C. with decomposition.

N-Benzyl-4-(3-hydroxy-4-methoxyphenyl)-1,2,3,6-tetrahydropyridine may be prepared in the following manner:

A solution of 2-benzyloxy-4-bromoanisole (4 g) in anhydrous tetrahydrofuran (25 cc) is added dropwise to a suspension of magnesium (0.33 g) in anhydrous tetrahydrofuran (5 cc) under reflux. When the addition is complete, refluxing is continued for 2 hours, and 4-benzyl-l-piperidone (2.5 g) dissolved in tetrahydrofuran (10 cc) is then added slowly, is refluxed for 1 hour and allowed to return to ambient temperature. After addition of a 1 N solution of hydrochloric acid (40 cc), the reaction mixture is extracted with ethyl ether (2×50 cc), and the aqueous phase is then made alkaline with a concentrated aqueous ammonia solution. After extraction with ethyl acetate (250 cc), the phases are separated and the organic phase is then washed with water and is dried over magnesium sulphate.

After filtration and concentration to dryness under reduced pressure (5.2 kPa), the yellow oil obtained is refluxed for 6 hours in the presence of concentrated hydrochloric acid (5 cc), water (10 cc) and ethanol (5 cc). The reaction mixture is then made alkaline with a concentrated solution of aqueous ammonia, and is then extracted with ethyl ether (2×100 cc). The ether phase is then washed with water (30 cc) and is then dried over magnesium sulphate. After filtration and concentration to dryness under reduced pressure (5.2 kPa), a brown oil (2.5 g) is obtained, which is then chromatographed on a column 5 cm in diameter, containing silica gel (32–63 μ; 100 g), using a cyclohexane-ethyl acetate mixture (50-50 by volume; 420 cc) as eluent and collecting 30 -cc fractions. The fractions between 240 cc and 420 cc are concentrated to dryness.

N-Benzyl-4-(3-hydroxy-4-methoxyphenyl)-1,2,3,6-tetrahydropyridine (0.75 g) is thus obtained in the form of a grey solid melting at 116°–119° C. 2-Benzyloxy-4-bromoanisole may be prepared according to the method described by Chaffee, Alanl et al., Austr. J. Chem., 34 (3), 587-98 (1981).

EXAMPLE 49

1-[2-(3,4-Dihydro-1(2H)-benzopyran-4-yl)ethyl]-4-(4-hydroxy-3-methoxyphenyl)piperidine is prepared by proceeding as in Example 48 but starting with 4-(4-hydroxy-3-methoxyphenyl)piperidine, 4-(2-bromoethyl)-3,4-dihydro-2H-benzopyran (0.49 g) and potassium iodide (0.5 g) in 2-butanone (35 cc).

The oil obtained is chromatographed on a column 3.3 cm in diameter, containing silica gel (100 g), using a methylene chloride-isopropanol mixture (95-5 by volume; 500 cc) as eluent and collecting 50-cc fractions. The fractions between 250 cc and 500 cc are concentrated to dryness.

The oil obtained is taken up with ethanol (10 cc) and oxalic acid (130 mg) dissolved in ethanol (2 cc) is added. After concentrating almost to dryness, a mixture of 2-butanone and isopropyl ether (50-50; 4 cc) is added and the mixture is heated until dissolved. After cooling, the crystals formed are filtered off and recrystallized from a 2-butanone-isopropyl ether mixture (50-50 by volume; 10 cc).

1-[2-(3,4-Dihydro-1(2H)-benzopyran-4-yl)ethyl]-4-(4-hydroxy-3-methoxyphenyl)piperidine hydrogen oxalate (0.48 g) is thus obtained in the form of a cream crystalline powder melting at 180° C.

4-(4-Hydroxy-3-methoxyphenyl)piperidine may be prepared in the following manner:

4-(4-Hydroxy-3-methoxyphenyl)-1,2,3,6-tetrahydropyridine (1.3 g) dissolved in acetic acid (150 cc) containing a solution (5.5N; 1.4 cc) of hydrochloric acid in isopropanol is hydrogenated under 5 atmospheres, in the presence of palladium on charcoal (10%; 0.26 g).

After filtration through sintered glass and concentration to dryness under reduced pressure (5.2 kPa), an oil (1.8 g) is obtained and is taken up with water (50 cc). The pH is adjusted to 8–9 by adding a sodium bicarbonate solution (0.5N). After extractions with a chloroform-isopropanol mixture (5-1 by volume; 5×200 cc), the organic phase is dried over magnesium sulphate and is then concentrated to dryness under reduced pressure.

The residue is chromatographed on a column 3.3 cm in diameter containing silica gel (100 g), using a mixture of toluene, ethanol and diethylamine (60-35-5 by volume; 1,300 cc) as eluent. The fractions between 580 cc and 1,300 cc are concentrated to dryness.

4-(4-Hydroxy-3-methoxyphenyl)piperidine (0.6 g) is thus obtained in the form of an orange solid melting at 208° C.

4-(4-Hydroxy-3-methoxyphenyl)-1,2,3,6-tetrahydropyridine may be prepared according to the method described by Wieslaw Gessner et al., J. Med. Chem., 28, 311–317 (1985).

EXAMPLE 50

The procedure is as in Example 48, but starting with 4-(2-bromoethyl)-2,2-dimethyl-3,4-dihydro-2H-benzopyran (0.4 g), 4-(4-hydroxy-3-methoxyphenyl)piperidine (0.5 g) and potassium iodide (0.25 g) in 2-butanone (35 cc).

The residue obtained is taken up with dichloromethane (100 cc) and the organic solution is then washed with a 20% strength solution of aqueous ammonia (30 cc) and then with water. The organic phase is then dried over magnesium sulphate and is concentrated to dryness under reduced pressure. The oil obtained is chromatographed on a column 3.3 cm in diameter containing silica gel (50 g), using a dichloromethane-ethanol mixture (25-5 by volume; 240 cc) as eluent and collecting 15-cc fractions. The fractions between 150 cc and 240 cc are concentrated to dryness.

Oxalic acid (125 mg) dissolved in ethanol (2 cc) is added to the residue obtained, dissolved in hot ethanol (10 cc). After concentration under reduced pressure until a paste is formed, the residue is taken up with hot 2-butanone (5 cc).

After cooling, the crystals formed are filtered off and 1-[2-(2,2-dimethyl-3,4-dihydro-1(2H)-benzopyran-4-yl)ethyl]-4-(4-hydroxy-3-methoxyphenyl)piperidine hydrogen oxalate (0.59 g) is obtained in the form of a white solid melting at 207° C.

EXAMPLE 51

The procedure is as in Example 22, but starting with 4-(2-bromoethyl)-2,2-dimethyl-3,4-dihydro-2H-benzopyran (2.5 g), 4-(4-methylsulphonamidophenyl)piperazine (2.37 g) and dry potassium carbonate (0.64 g), followed by potassium iodide (1.54 g) in 2-butanone (80 cc).

After evaporation of the solvent, the oil obtained is taken up with water (40 cc) and is then extracted with dichloromethane (200 cc). The organic phase is then dried over magnesium sulphate. After evaporation, the residue obtained is chromatographed on a column 3.3 cm in diameter, containing silica gel (100 g), using a dichloromethane-ethanol mixture (95-5 by volume; 900 cc) as eluent, and collecting 30-cc fractions. The fractions between 190 cc and 850 cc are concentrated to dryness.

The oil obtained is taken up with methanol (40 cc) and a solution (5.5N) of hydrochloric acid (2.4 cc) is added.

After concentration to dryness and recrystallization from ethanol (100 cc), 1-[2-(2,2-dimethyl-3,4-dihydro-1(2H)-benzopyran-4-yl)ethyl]-4-(4-methylsulphonamidophenyl)piperazine hydrochloride (1.77 g) is obtained in the form of white crystals melting with decomposition at 200° C.

4-(4-Methylsulphonylaminophenyl)piperazine may be prepared according to patent application EP No. 244,115.

EXAMPLE 52

4-(2-Bromoethyl)-6-nitro-3,4-dihydro-2H-benzopyran (0.6 g), 4-(4-methylsulphonamidophenyl)piperazine (0.535 g) and dry potassium carbonate (0.145 g), followed by potassium iodide (0.35 g) in 2-butanone (30 cc), are refluxed for 12 hours.

The reaction mixture is filtered through sintered glass and the solvent is then evaporated off under reduced pressure (5.2 kPa).

The residue obtained is taken up with a bicarbonate solution (M; 10 cc) and is then extracted with ethyl acetate (2×50 cc). The organic phase is then washed with water and then dried over magnesium sulphate.

After filtration and evaporation of the solvent, a yellow resin is obtained, which is purified by flash chromatography on a column 5 cm in diameter containing silica gel (40–60 μ; 110 g), using a dichloromethane-isopropanol mixture (95-5 by volume) as eluent and collecting 30-cc fractions. The fractions between 180 cc and 360 cc are concentrated to dryness.

1-(4-Methylsulphonamidophenyl)-4-[2-(6-nitro-3,4-dihydro-1(2H)-benzopyran-4-yl)ethyl]piperazine (0.75 g) is thus obtained in the form of a yellow solid melting in the neighbourhood of 68° C.

EXAMPLES 53

4-(2-Bromoethyl)-6-nitro-3,4-dihydro-2H-benzopyran (0.6 g), 1-(4-hydroxy-3-methoxyphenyl)piperidine (0.8 g) and potassium iodide (0.34 g) in 2-butanone (35 cc) are refluxed for 16 hours.

The reaction mixture is filtered through sintered glass and the solvent is then evaporated off under reduced pressure (5.2 kPa). The residue obtained is taken up with a 20% strength solution of aqueous ammonia (20 cc) and is then extracted with dichloromethane (100 cc). The organic phase is then washed with water and then dried over magnesium sulphate.

After filtration and evaporation of the solvent, a brown oil is obtained, which is purified by chromatography on a column 3 cm in diameter containing silica gel (40–60 μ; 50 g), using a dichloromethaneethanol mixture (95-5 by volume) as eluent and collecting 10-cc fractions. The fractions between 140 cc and 250 cc are concentrated to dryness.

1-(4-Hydroxy-3-methoxyphenyl)-4-[2-(6-nitro-3,4-dihydro-1(2H)-benzopyran-4-yl)ethyl]piperazine (0.6 g) is thus obtained in the form of a light-brown oil.

Proton NMR spectrum (250 MHz, CDCl₃, δ in ppm):

| | | |
|---|---|---|
| 6.75 (dd | ⎫ 2H | ⎫ |
| 6.77 (d | ⎭ | ⎬ phenyl aromatic) |
| 6.87 (d, | 1H | ⎭ |
| 6.87 (d, | 1H, | aromatic at 8) |
| 8.01 (dd, | 1H, | aromatic at 7) |
| 8.19 (d, | 1H, | aromatic at 5) |
| 4.32 (mt, | 2H, | —O—C$\underline{H}_2$—) |
| 3.89 (s, | 3H, | —O—C$\underline{H}_3$) |

3.11 and 3.0 (mt, $>$C$\underline{H}$— of benzopyran, one of the Hs in

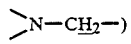

2.5 (mt, the other H in $>$N—C$\underline{H}_2$—)

1.65 to 2.15 (mt, —C$\underline{H}_2$— and $>$C$\underline{H}$—C₆H₃(OH)(OCH₃)).

EXAMPLE 54

1-[2-(3,4-Dihydro-1(2H)-benzopyran-4-yl)ethyl]-4-(3,4-dimethoxyphenyl)piperidine hydrochloride (6.75 g) is heated to 90° C. for 18 hours in acetic acid (100 cc) to which concentrated hydrobromic acid (100 cc) has been added.

The reaction mixture is then concentrated to dryness under reduced pressure (5.2 kPa) and the residue obtained is crystallized by addition of a mixture of ethyl ether and 2-butanone (50-50 by volume).

The crystals formed are then taken up with a minimum quantity of hot ethanol, and ethyl ether is then added until brown resins are formed, which are removed by filtration.

After cooling of the filtrate, 1-[2-(3,4-dihydro-1(2H)-benzopyran-4-yl)ethyl]-4-(3,4-dihydroxyphenyl)piperidine hydrobromide (3.24 g) is obtained in the form of a white solid melting at 187° C.

EXAMPLE 55

The procedure is as in Example 38, but starting with 1-(4-methylsulphonamidophenyl)-4-[2-(6-nitro-3,4-dihydro-1(2H)-benzopyran-4-yl)ethyl]piperazine (0.74 g) in absolute ethanol (65 cc) to which an isopropanol solution (5.5N; 0.58 cc) of hydrochloric acid has been added, and in the presence of palladium on charcoal (10%; 0.37 g).

After hydrogenation, the mixture is concentrated under reduced pressure (5.2 kPa) and the oil obtained is taken up with a 20% strength solution of aqueous ammonia (100 cc).

After extraction with ethyl acetate (2×100 cc), the organic phase is separated off and is then dried over magnesium sulphate.

After evaporation, the oil obtained is chromatographed on a column 5 cm in diameter containing silica gel (40–63 μ; 100 g), using a toluene-ethanoldiethylamine mixture (82-15.5-2.5 by volume; 870 cc) as eluent and collecting 30-cc fractions. The fractions between 480 cc and 870 cc are concentrated to dryness. The viscous oil obtained is dissolved in hot ethanol (20 cc) and a solution of oxalic acid (0.134 g) in ethanol (3 cc) at 40° C. is added to it.

After cooling, the crystals formed are filtered off and 4-[2-(6-amino-3,4-dihydro-1(2H)-benzopyran-4-yl)ethyl]-1(4-methylsulphonamidophenyl)piperazine hydrogen oxalate (0.25 g) is thus obtained in the form of beige crystals melting at 138° C.

EXAMPLE 56

The procedure is as in Example 38, but starting with 1-(4-hydroxy-3-methoxyphenyl)-4-[2-(6-nitro-3,4-dihydro-1(2H)-benzopyran-4-yl)ethyl]piperazine (0.6 g) in absolute ethanol (200 cc), to which a hydrochloric acid solution (5.5N; 1.4 cc) has been added, and in the presence of palladium on charcoal (10%; 0.3 g). After hydrogenation, the mixture is concentrated under reduced pressure (5.2 kPa) and the oil obtained is taken up with a 20% strength solution of aqueous ammonia (20 cc). After extraction with dichloromethane (2×100 cc), the organic phase is dried over magnesium sulphate.

After evaporation of the solvent, the oil obtained is chromatographed on a column 3 cm in diameter containing silica gel (40–63 μ; 60 g), using an ethyl acetate-ethanol-20% strength aqueous ammonia solution mixture (95-3-2 by volume; 1,600 cc) as eluent and collecting 25-cc fractions. The fractions between 550 cc and 1,600 cc are concentrated to dryness and extracted with dichloromethane. After washing repeatedly with water, the organic phase is dried over magnesium sulphate and is then concentrated to dryness.

The viscous oil obtained is dissolved in hot methanol (10 cc) and a solution of oxalic acid (0.083 g) in methanol (2 cc) at 40° C. is added to it.

After concentration under reduced pressure (5.2 kPa) to approximately 1 cc, the residue is taken up with hot 2-butanone (20 cc). The brown resins formed are removed by phase separation. Isopropyl ether (10 cc) is then added. After cooling and scratching, 1-[2-(6-amino-3,4-dihydro-1(2H)-benzopyran-4-yl)ethyl]-4-(4-hydroxy-3-methoxyphenyl)piperazine hydrogen oxalate (0.180 g) is obtained in the form of greyish crystals melting in the neighbourhood of 145° C.

The present invention also relates to the pharmaceutical compositions consisting of a product of general formula (I) in free form or in the form of an addition salt with a pharmaceutically acceptable acid, in pure form or in the form of a combination with any other pharmaceutically compatible product, which may be inert or physiologically active. The compositions according to the invention may be employed orally or parenterally.

Tablets, pills, powders or granules may be employed as solid compositions for oral administration. In these compositions, the active product according to the invention (optionally combined with another pharmaceutically compatible product) is mixed with one or more inert diluents or adjuvants such as sucrose, lactose or starch. These compositions may also contain substances other than the diluents, e.g. a lubricant such as magnesium stearate.

Pharmaceutically acceptable emulsions, solutions, suspensions, syrups and elixirs containing inert diluents such as water or liquid paraffin may be employed as liquid compositions for oral administration. These compositions may also contain substances other than the diluents, e.g. wetting products, sweeteners or flavourers.

The sterile compositions for parenteral administration may be preferably aqueous or nonaqueous solutions, suspensions or emulsions. Water, propylene glycol, a polyethylene glycol, vegetable oils, especially olive oil, injectable organic esters, e.g. ethyl oleate or other suitable organic solvents may be employed as a solvent or carrier. These compositions may also contain adjuvants, in particular wetting, isotonizing, emulsifying, dispersing and stabilizing agents. The sterilization may be effected in a number of ways, e.g. by aseptifying filtration, by incorporating sterilizing agents into the composition, by irradiation or by heating. They may also be prepared in the form of sterile solid compositions which may be dissolved at the time of use in an injectable sterile medium.

The pharmaceutical compositions according to the invention are particularly useful in human therapeutics by reducing cardiac rhythm disorders due to treated or untreated reentry phenomena in the treatments following the myocardial infarction, and in chronic anginal states and cardiopathies of an ischaemic type.

In general, the practitioner will determine the dosage which he considers the most suitable as a function of the age, the weight and the other factors specific to the subject to be treated.

The dosages are generally of between 0.25 and 1.5 g of active product daily, orally or intravenously in the case of an adult.

The following example, given without any limitation being implied, illustrates a composition according to the invention.

EXAMPLE

Tablets having the following composition are prepared:

| | |
|---|---|
| 1-[2-(3,4-dihydro-1(2H)-benzopyran-4-yl)ethyl]-4-(3,4-dimethoxyphenyl)piperidinehydrochlorede | 136.7 mg |
| lactose | 50 mg |
| excipient q.s. | 250 mg |

We claim:
1. A benzopyran derivative of the formula:

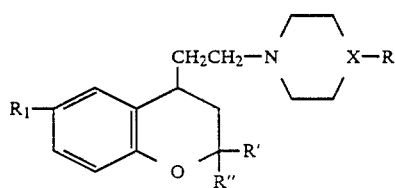

in which
- R₁ is hydrogen, halogen, hydroxy, alkoxy, nitro, amino, alkylsulphonamido, bis(alkylsulphonyl)amino or acylamino,
- X denotes a nitrogen atom or a >CH—radical,
- R is a radical of formula:

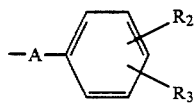

in which A is a single bond, methylene or (when X is a nitrogen atom) carbonyl, and $R_2$ and $R_3$, which are identical or different, are hydrogen, halogen, hydroxy, alkyl, alkoxy, nitro, amino, alkylsulphonamido, bis(alkylsulphonyl)amino, acylamino, sulphamoyl or cyano, or $R_2$ and $R_3$, when they are adjacent, together form a methylenedioxy or ethylenedioxy radical, or else
R is pyridyl or 2(2H)-benzimidazolonyl if X denotes >CH—, and R' and R" are identical and are hydrogen or alkyl, the aforesaid alkyl and acyl radicals containing 1 to 4 carbon atoms each in a straight or branched chain, and its isomeric forms and mixtures thereof, and its acid addition salts.

2. A benzopyran derivative according to claim 1, wherein
- R₁ is hydrogen, chlorine, fluorine, hydroxy, methoxy, nitro, amino or methylsulphonamido,
- X denotes a nitrogen atom or a >CH—radical,
- R is a radical of formula:

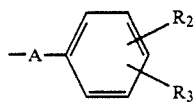

in which A is a single bond, methylene or (when X is a nitrogen atom) a carbonyl, and $R_2$ and $R_3$, which are identical or different, are situated in the 3 and/or 4 position and are hydrogen, fluorine, hydroxy, methyl, methoxy, nitro, amino, methylsulphonamido, bis(methylsulphonyl)amino, acetamido, sulphamoyl or cyano, or $R_2$ and $R_3$, when they are adjacent, together form a methylenedioxy or ethylenedioxy radical, or else
R is pyridyl or 2(2H)-benzimidazolonyl if X denotes >CH—, and
R' and R" are identical and are hydrogen or methyl, and its isomeric forms and mixtures thereof, and its acid addition salts.

3. A benzopyran according to claim 1 which is 1-[2-(3,4-dihydro-1(2H) -benzopyran-4-yl)ethyl]-4-(3,4-dimethoxyphenyl) piperidine, its isomeric forms and mixtures thereof, and its acid addition salts.

4. A benzopyran according to claim 1 which is 1-[2-(6-amino-3,4dihydro-1(2H)-benzopyran-4-yl )-ethyl]-4-(3,4-dimethoxyphenyl) piperidine, its isomeric forms and mixtures thereof, and its acid addition salts.

5. A benzopyran according to claim 1 which is 1-[2-(3,4-dihydro-1(2H)-benzopyran-4-yl)ethyl]-4-(4-methylsulphonamidophenyl)piperidine, its isomeric forms and mixtures thereof, and its acid addition salts.

6. A benzopyran according to claim 1 which is 1[2-(3,4-dihydro-1(2H)-benzopyran-4-yl)ethyl]-4-(4-methysulphonamidophenyl) piperazine, its isomeric forms and mixtures thereof, and its acid addition salts.

7. A benzopyran according to claim 1 which is 1-{1-[2-(3,4-dihydro-1(2H)-benzopyran-4-yl)ethyl]-4-piperidinyl}-1,3-dihydro-2(2H) -benzimidazolone, its isomeric forms and mixtures thereof, and its acid addition salts.

8. A pharmaceutical composition which comprises a benzopyran derivative according to claim 1, in combination with a compatible and pharmaceutically acceptable diluent or adjuvant.

9. Method of reducing a cardiac rhythm disorder which comprises administering to a subject suffering from such disorder an effective amount of a benzopyran derivative according to claim 1.